United States Patent

Hu et al.

[11] Patent Number: 5,886,264
[45] Date of Patent: Mar. 23, 1999

[54] SYSTEM AND METHOD FOR PREDICTING SOUND RADIATION AND SCATTERING FROM AN ARBITRARILY SHAPED OBJECT

[75] Inventors: Quiang Hu, Detroit; Sean F. Wu, Troy, both of Mich.

[73] Assignee: Wayne State University, Detroit, Mich.

[21] Appl. No.: 851,510

[22] Filed: May 5, 1997

[51] Int. Cl.$^6$ .............................. G01H 1/00; G01N 29/00
[52] U.S. Cl. ................................ 73/646; 73/657; 356/28; 128/660.01
[58] Field of Search .............................. 73/646, 657, 656, 73/645; 367/90, 94, 904; 356/27, 28; 340/554, 555, 556, 557; 128/660.01, 660.02

[56] References Cited

U.S. PATENT DOCUMENTS

| | | | |
|---|---|---|---|
| 3,738,750 | 6/1973 | Kalb et al. .............................. | 356/28 |
| 4,655,086 | 4/1987 | Mielnicka-Pate et al. ............... | 73/646 |
| 5,086,775 | 2/1992 | Parker et al. ........................... | 600/453 |
| 5,099,848 | 3/1992 | Parker et al. ........................... | 600/443 |

*Primary Examiner*—Hezron Williams
*Assistant Examiner*—Richard A. Moller
*Attorney, Agent, or Firm*—Howard & Howard

[57] ABSTRACT

An alternate formulation is derived for predicting acoustic radiation from a vibrating object in an unbounded fluid medium. The radiated acoustic pressure is shown to be expressible as a surface integral of the particle velocity, which is determinable by using a non-intrusive laser Doppler velocimeter. Solutions thus obtained are unique. Moreover, the efficiency of numerical computations is high because the surface integration can be readily implemented numerically by using the standard Gaussian quadratures. This alternate formulation can be desirable for analyzing the acoustic and vibration responses of a lightweight, a flexible or a structure with a hostile environment for which a non-intrusive laser measurement technique must be used.

18 Claims, 9 Drawing Sheets ptl
SYSTEM AND METHOD FOR PREDICTING SOUND RADIATION AND SCATTERING FROM AN ARBITRARILY SHAPED OBJECT This invention was made with government support under Agreement No. CMS-9414424 by the National Science Foundation. The government has certain rights in the invention.

BACKGROUND OF THE INVENTION

A. Background

The Kirchhoff integral formulation is one of the most widely used methods for predicting acoustic radiation and scattering from an elastic structure in engineering practice. The advantage of using this integral formulation is a reduction of the dimensionality of the problem by one. The first step of this approach is to determine the acoustic quantities on the surface. For an acoustic radiation problem, the normal component of the particle velocity (or the surface acoustic pressure for an acoustic scattering problem) must be specified. Since the surface is impermeable, the normal component of the particle velocity is equal to that of the surface velocity, which can be measured by an accelerometer. Next, the surface acoustic pressure (or the normal component of the particle velocity for acoustic scattering) is determined by solving an integral equation. Once these quantities are known, the radiated acoustic pressure anywhere can be calculated by the Kirchhoff integral formulation.

It may be difficult to use a conventional accelerometer to measure the vibration response of a flexible or a lightweight structure such as a loudspeaker membrane or a passenger vehicle fuel pump, because the weight of the accelerometer may alter the desired signal. In other cases, it may be unfeasible to use an accelerometer on a structure with a hostile environment such as an engine oil pan, where the temperature on the surface is extremely high. Under these circumstances, we must rely on a non-intrusive measurement technique.

One approach commonly adopted in practice is to use a laser vibrometer to measure the normal component of the particle velocity, which is equal to that of the surface velocity at the interface, and then solve an integral equation for the surface acoustic pressure. The shortcomings of such an approach are well-known: (1) the surface Kirchhoff integral equation may fail to yield a unique solution whenever the frequency is close to one of the eigenfrequencies associated with to the related interior boundary value problem, and (2) the numerical computation may become quite involved. This is because for an arbitrary surface, we must discretize the surface into many segments with several hundreds or even more nodes. Accordingly, we must solve a large number of simultaneous integral equations for the acoustic pressures at these nodes using boundary element method (BEM). Since the central processing unit (CPU) time increases quadratically with the number of the nodes, the computation process may be excessively time-consuming.

Actually, the laser technique can be used to measure the displacement and velocity vectors of a suspended micropar-ticle in an insonified medium. The work in this area, however, has received much less attention than that of measurements of the out-of-plane motion of a vibrating structure. Summarized below are the basic principles and applications of the non-intrusive laser measurement techniques to measurements of the particle displacement and velocity vectors both in fluids and in air.

B. Laser techniques

1. Laser Doppler velocimeter (LDV)

LDV has become a standard tool for non-intrusive measurements of fluid particle velocities. The basic premise in the LDV measurements is that motion of the microparticles in the fluid (either due to natural impurities or due to seeded particles) will scatter the incident light, and produce a Doppler shift in the scattered light which can be detected with appropriate electronics and signal processing. LDV used in the fluid mechanics was extended to the acoustics by measuring the in-air particle velocities associated with steady-state time-harmonic standing waves and travelling waves inside a tube. Laser Doppler anemometry (LDA) has been used for the remote detection of sound. The technique of LDA consists of measurements of the velocity of neutrally buoyant microparticles suspended in an acoustic field by analyzing the spectral content of Doppler-shifted laser light scattered by the microparticles. LDV has been used to measure the acoustic particle velocity in fluids. In particular, the measurements of acoustic particle displacements using different LDV systems has determined that LDV was capable of detecting the particle displacements in the order of a few nanometers with a bandwidth of several kilohertz. The performance and limitations of LDV systems were also analyzed, and the effect of Brownian motion (i.e., thermal agitation in the fluid) on the measured data was shown to produce only negligible broadening of the spectral density of the signal of interest. An equation of motion of microparticles in suspension in an insonified fluid has been derived and it has been determined that the motion of neutrally buoyant microparticles closely emulates the displacement of the surrounding insonified fluid and confirms the basic tenet associated with the laser detection of sound.

2. Differential laser Doppler interferometry (DLDI)

DLDI is evolved from the principle of LDA and used to measure simultaneously the out-of-plane and the in-plane velocities on the surface of a vibrating object. The principle of DLDI is to measure the phase shift of the reflected or scattered light from the surface due to surface vibrational motion. The main component of a DLDI system is a probe head that has three illuminating single mode fibers. Prior to launching, the laser beams are frequency shifted by three acousto-optic Bragg cells by 40.0, 40.1, and 40.3 MHz, respectively, so the interference between the first and second beams occurs at 100 kHz, while those between the second and third and the first and third occur at 200 and 300 kHz, respectively. Geometrically, the first and second beams are positioned symmetrically with respect to the unit normal on the surface at an angle $\alpha$, and the third beam is aligned with the first and second beams at an angle $\beta(\beta<\alpha)$ with respect to the unit normal. In the differential configuration, the 100 kHz carrier will be modulated by the in-plane motion, and the 200 and 300 kHz carriers will be modulated by both in-plane and out-of-plane motions, respectively.

Mathematically, the surface displacement vector can be written as $$\vec{x}_s(t) = u_{in}(t)\vec{e}_{in} + u_{out}(t)\vec{e}_{out} \tag{1}$$

where $u_{in}(t)$ and $u_{out}(t)$ represent the in-place and out-of-place components of the surface displacement, respectively, and $\vec{e}_{in}$ and $\vec{e}_{out}$ are the unit vectors in the corresponding directions.

Accordingly, the phase terms $\phi_{ij}$, where i, j=1 to 3, in the 100, 200, and 300 kHz carriers can be written as $$\phi_{12} = 2ku_{in}(t)\sin\alpha \tag{2a}$$

$\phi_{13}=(\sin \alpha+\sin \beta)ku_{in}+(\cos \beta-\cos \alpha)ku_{out}(t)$ (2b)

$\phi_{23}=(\sin \alpha+\sin \beta)ku_{in}-(\cos \beta-\cos \alpha)ku_{out}(t)$ (2c)

where k is the optical wavenumber. Hence by measuring the phase shifts $\phi_{ij}$ in the 100, 200, and 300 kHz carriers, one can determine the displacement vector on the surface. Since there are only two unknowns, one can use any two equations, say, Eqs. (2a) and (2b) to specify $u_{in}$ and $u_{out}$.

In one optical system, the demodulation is done by using a combination of filters and the phase-locked loops (PLL). The PLL demodulates the signal with phase $\phi_{ij}$ and generates an output which is proportional to the time rate of changes of $\phi_{ij}$. From Eqs. (2a) and (2b), one finds $$\frac{du_{in}(t)}{dt} = \frac{1}{2k\sin\alpha} \frac{d\phi_{12}}{dt}$$ (3a)

$$\frac{du_{out}(t)}{dt} = \frac{1}{k(\cos\beta-\cos\alpha)} \left[ \frac{d\phi_{13}}{dt} - \frac{(\sin\alpha+\sin\beta)}{2\sin\alpha} \frac{d\phi_{12}}{dt} \right]$$ (3b)

Therefore, by measuring the instantaneous frequency deviations $d\phi_{12}/dt$ and $d\phi_{13}/dt$ from the carrier frequencies at 100 and 300 kHz, one can determine simultaneously the in-plane and out-of-plane components of the surface velocity. A three dimensional laser vibrometer was designed based on this principle to measure simultaneously the three components of the velocity on the surface of a vibrating structure.

The DLDI technique can be extended in principle to the measurement of the velocity of a microparticle in the vicinity of a vibrating object. Imagine that an object is surrounded by neutrally buoyant microparticles. As the object vibrates, the acoustic pressure fluctuations will excite the microparticles into oscillations. Suppose that we define a control surface and focus the laser beams on a microparticle lying on that surface. There is no restriction on the formation of the control surface so long as it completely encloses the vibrating object. In the special case in which the control surface coincides with the vibrating surface, the normal component of the displacement of the microparticle will be equal to that of the surface displacement, while the tangible components may be different. In any event, the microparticle displacement in the directions normal and tangential to the control surface will cause a Doppler shift in the phase $\phi_{ij}$ of the reflected light, which is modulated in the frequency carriers. Once the signal with phase $\phi_{ij}$ is demodulated, we can calculate the microparticle velocity which is proportional to the time derivative of the phase, $d\phi_{ij}/dt$.

3. Electronic speckle pattern interferometry (ESPI)

Alternatively, we can use ESPI to measure the phase term of a microparticle, which is an established optical technique for measuring static and dynamic deformations and surface shapes for more than two decades. Specifically, we can utilize the stroboscopic technique, which "freezes" the dynamic motion of a particle at one position so that during other times of the movement cycle, the particle is not illuminated and therefore is "invisible" to the imaging device. In practice, this technique can be implemented by using a pulsed laser or a light shuttering device with a continuous wave laser. The time interval between two consecutive pulses or shutters is typically in the range of nanoseconds, so ESPI can capture very high frequency oscillations. By using an additive-subtractive speckle pattern interferometry, the accuracy of the phase measurement can be further enhanced.

Suppose that we take five frames of additive speckle patterns of the motion of a microparticle in suspension $S_j$, j=0, 1 ..., and 4. Here the speckle pattern $S_o$ is taken with the laser illumination pulsed at the instant when the microparticle reaches its zero amplitude of a harmonic oscillation. The remaining four speckle patterns, $S_1$ to $S_4$, are taken with the laser illumination pulsed at the instants when the microparticle reaches its maximum and minimum amplitudes. During the acquisition of $S_0$ to $S_4$, the phase of the reference beam is shifted appropriately and is synchronized with the pulses. Accordingly, the displacement-induced phase term $\phi$ of a microparticle at any surface point $\vec{x}_s$ can be written as $$\phi = \tan^{-1}\left(\frac{F_1-F_3}{F_2-F_0}\right)$$ (4)

where $F_n$, n=0, 1, 2, and 3, are the additive-subtractive fringe patterns which have the same form as that of the Michelson interferometric fringe pattern, except for the randomly distributed modulation term $B/\cos \psi/$ contributed by the speckles, $$F_n=B|\cos \psi|[1-\cos (\phi+n\pi/2)]$$ (5)

Once the phase term $\phi$ is determined, the microparticle velocity which is proportional to the time derivative of the phase can be specified.

SUMMARY OF THE INVENTION

The present invention provides an explicit integral formulation for predicting acoustic radiation and scattering from an object of arbitrary shape. The radiated acoustic pressure is shown to be expressible as integrations of normal and tangential components of the particle velocity at the surface of a vibrating object, which are determined by a non-intrusive laser Doppler velocimeter.

The present invention is readily extensible to transient acoustic radiation. Since the acoustic pressure is expressed as an explicit function of the velocity distribution, one can use the Fourier transformation to obtain the acoustic pressure in the frequency domain first, and then take an inverse Fourier transformation to get the time-domain signal.

As illustrative examples only, the present invention can be utilized to predict acoustic radiation from automotive components, vehicle interior noise, the acoustic radiation from a vehicle as perceived by a stationary observer, sound radiation from submarines, etc.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DETAILED DESCRIPTION OF A PREFERRED EMBODIMENT

Figure 1:
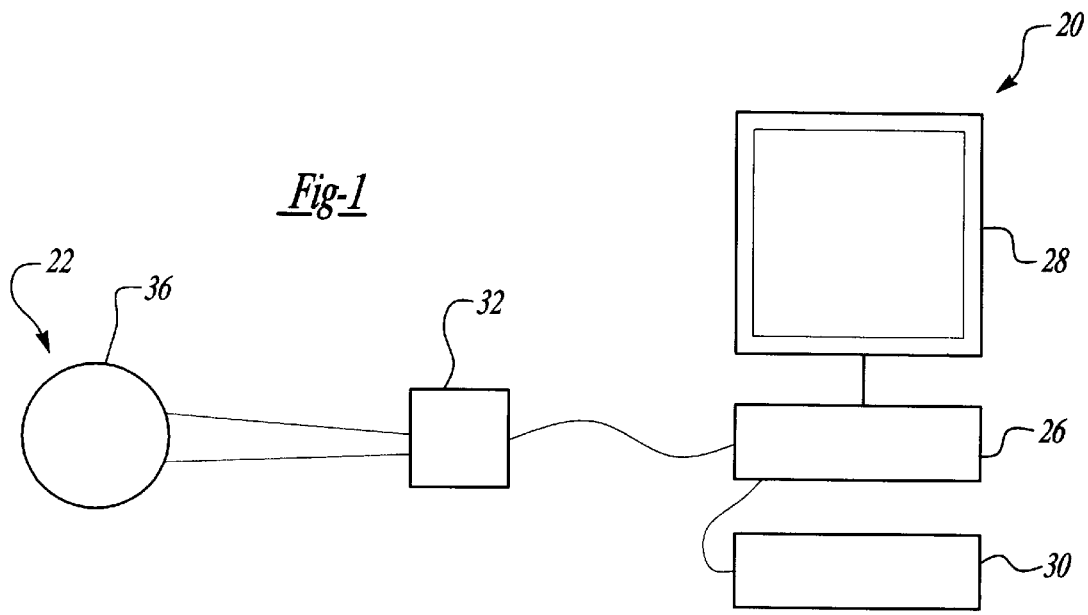
FIG. 1 is a schematic of the system for predicting sound radiation from a vibrating object of the present invention.
Figure 2:
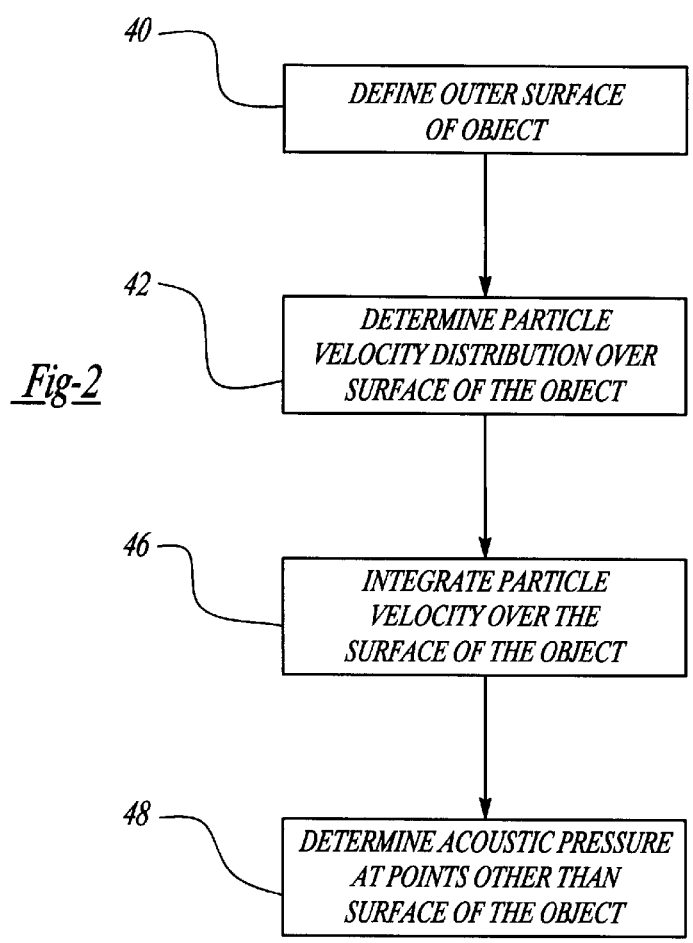
FIG. 2 is a flowchart of the method of predicting sound radiation from a vibrating object of the present invention.

The present invention provides a system 20 for predicting acoustic radiation and scattering from an object 22 of arbitrary shape. A spherical object 22 is shown only for illustrative purposes. It will be demonstrated that the system 20 of the present invention is useful for objects 22 of arbitrary shape.

The system 20 preferably includes a CPU 26 having a monitor 28 and keyboard 30 or other input device. Further, as will be explained later, the system 20 may further include an accelerometer 32, which is preferably a non-intrusive laser Doppler velocimeter 32.

In operation, the shape, i.e. outer surface 36 of the object 22 is defined mathematically and input into the CPU 26 in step 40. This can be accomplished utilizing input device 30, CAD models, or imaging techniques, all of which are well known in the art. The particle velocity distribution over the surface 36 of the vibrating object 22 is then measured by a non-intrusive laser Doppler velocimeter 32 and input into the CPU 26 in step 42. Alternatively, the particle velocity distribution over the surface of the vibrating object 22 can be described mathematically and input into CPU 26 utilizing the input device 30.

In step 46, the CPU 26 integrates the particle velocity over the surface 36 of the vibrating object 22. In step 48, the CPU 26 determines the acoustic pressure at a point other than that the surface 36 of the vibrating object 22. As will be described below, this point could be interior or exterior to the surface 36 of the vibrating object 22.

The present invention provides an alternate formulation which enables one to predict the radiated acoustic pressure directly, once the particle velocity at the interface of a vibrating surface is determined by a non-intrusive laser Doppler velocimeter. The significance of this alternate formulation is two-fold: (1) solutions thus obtained are unique and (2) the efficiency of numerical computations is high. This is because in this alternate formulation, the radiated acoustic pressure is expressed as a surface integral of the particle velocity that can be implemented numerically using the standard Gaussian quadratures. There is no need to use BEM to solve a set of simultaneous integral equations for the surface acoustic pressures at the discretized nodes, which can be time-consuming for an arbitrarily shaped object. Such an approach can be desirable for analyzing the acoustic and vibration responses of the structure which requires the use of a non-intrusive laser measurement technique.

I. BASIC THEORY

Consider sound radiation from a finite object immersed in an unbounded fluid medium with density $\rho_o$ and sound speed c. Assume that the object vibrates at a constant frequency $\omega$, so an acoustic quantity can be written as a complex amplitude multiplied by a time dependence of $e^{-i\omega t}$. In this way, the complex amplitude of the radiated acoustic pressure $\hat{p}(\vec{x})$ at any point $\vec{x}$ can be written as $$\hat{p}(\vec{x}) = \frac{1}{4\pi} \int_S \left[ \frac{\partial G(\vec{x}|\vec{x}_S)}{\partial n_S} \hat{p}(\vec{x}_S) - G(\vec{x}|\vec{x}_S) \frac{\partial \hat{p}(\vec{x}_S)}{\partial n_S} \right] dS \quad (6)$$

where G and $\partial G/\partial n$ are the free-space Green's function and its normal derivative given, respectively, by $$G(\vec{x}|\vec{x}_S) = \frac{e^{ikR}}{R} \text{ and } \frac{\partial G(\vec{x}|\vec{x}_S)}{\partial n_S} = \frac{(ikR-1)e^{ikR}}{R^2} \frac{\partial R}{\partial n_S} \quad (7)$$

where $n_S$ stands for the outward unit normal on the surface S and $R=|\vec{x}-\vec{x}_S|$, here $\vec{x}$ and $\vec{x}_S$ represent the receiver and source position vectors, respectively.

Equation (6) is an integral representation of the Helmholtz equation in the frequency domain. The normal derivative of the acoustic pressure on the right side of Eq. (6) is related to the normal component of the particle velocity $\hat{v}_n(\vec{x}_S)$, which is equal to that of the surface velocity at the interface. For an acoustic radiation problem, the normal component of the surface velocity is specified. Hence, one must solve an integral equation obtained by letting the field point $\vec{x}$ in Eq. (6) approach the surface to determine the surface acoustic pressure $\hat{p}(\vec{x}_S)$ $$\hat{p}(\vec{x}_S) = \frac{1}{2\pi} \int_S \left[ \frac{\partial G(\vec{x}'_S|\vec{x}_S)}{\partial n_S} \hat{p}(\vec{x}_S) - i\omega\rho_0\hat{v}_n(\vec{x}_S)G(\vec{x}'_S|\vec{x}_S) \right] dS \quad (8)$$

where R is replaced by $R_S=|\vec{x}'_S-\vec{x}_S|$, here both $\vec{x}'_S$ and $\vec{x}_S$ are on the surface S. For an arbitrary surface, there is no closed-form solution to Eq. (8) and $\hat{p}(\vec{x}_S)$ must be solved numerically by using BEM. Once $\hat{p}(\hat{x}_S)$ and $\hat{v}_n(\vec{x}_S)$ are all specified, the radiated acoustic pressure $\hat{p}(\vec{x})$ can be calculated by Eq. (6).

II. AN ALTERNATE FORMULATION

A formulation according to the present invention predicts the radiated acoustic pressure directly once the particle velocity at the interface is specified by a non-intrusive laser Doppler velocimeter. For completeness, we give formulations for both exterior and interior regions, respectively.

A. Exterior problems

Derivations of the alternate formulation start from the Euler equation, $$\nabla \hat{p}(\vec{x}) = i\omega\rho_0 \vec{v}(\vec{x}) \quad (9)$$

Integrating both sides of Eq. (9) along a line which connects one field point $\vec{x}'$ to another $\vec{x}$ yields $$\int_{(\vec{x}' \to \vec{x})} \nabla \hat{p}(\vec{x}) \cdot \vec{e} dl = \int_{(\vec{x}' \to \vec{x})} d\hat{p}(\vec{x}) = i\omega\rho_0 \int_{(\vec{x}' \to \vec{x})} \hat{\vec{v}}(\vec{x}) \cdot \vec{e} dl \quad (10)$$

where $\vec{e}$ is a unit vector in the direction of the line integral from $\vec{x}'$ to $\vec{x}$.

Obviously, the integral of $d\hat{p}(\vec{x})$ on the left side of Eq. (10) is determined by its upper and lower limits, but independent of the choice of the integration path. Hence, we obtain $$\hat{p}(\vec{x}) = \hat{p}(\vec{x}') + i\omega\rho_0 \int_{(\vec{x}' \to \vec{x})} \hat{\vec{v}}(\vec{x}) \cdot \vec{e} dl \quad (11)$$

Equation (11) shows that the complex amplitude of the acoustic pressure at any point $\vec{x}$ can be expressed as the sum of the complex amplitude of the acoustic pressure at another point $\vec{x}'$ plus a line integral of the apparent force per unit volume over any path that connects these two points. Since there is no restriction on the selection of the integral path, we choose to let it lie on the control surface $S_c$. Accordingly, we can write $$\hat{p}(\vec{x}_{s_c}) = \hat{p}(\vec{x}'_{s_c}) + i\omega\rho_0 \int_{(\vec{x}'_{s_c} \to \vec{x}_{s_c})} [\hat{v}_n(\vec{x}_{s_c}) dn + \hat{v}_\eta(\vec{x}_{s_c}) d\eta] \quad (12)$$

where $\hat{v}_n$ and $\hat{v}_\eta$ represent the normal and tangential components of the particle velocity at the surface $S_c$, respectively, and $dn$ and $d\eta$ are the increments in the normal and tangential directions on $S_c$, respectively. In the special case where the control surface coincides with the real surface, the normal component of the particle velocity $\hat{v}_n(\vec{x}_s)$ is equal to that of the surface velocity, but its tangential component $\hat{v}_\eta$ may be different.

Without loss of generality, we will omit the subscript c on $S_c$ in the following. Since the integration path remains perpendicular to the unit normal $\vec{n}$ at all times, $dn=0$. Hence the first term in the square brackets on the right side of Eq. (12) is identically zero, $$\hat{p}(\vec{x}_s) = \hat{p}(\vec{x}'_s) + i\omega\rho_0 \int_{(\vec{x}'_s \to \vec{x}_s)} \hat{v}_\eta(\vec{x}_s) d\eta \quad (13)$$

Substitute $\hat{p}(\vec{x}_s)$ into Eq. (8) and notice that $\hat{p}(\vec{x}'_s)$ represents the acoustic pressure at a fixed surface point $\vec{x}'_s$, which is independent of the integration with respect to the unprimed surface coordinates and therefore can be factored out of the integral sign. Combining the coefficients of $\hat{p}(\vec{x}'_s)$ on both sides of Eq. (8) yields a solution for $\hat{p}(\vec{x}'_s)$, which when substituted back into Eq. (13) gives a solution for $\hat{p}(\vec{x}_s)$.

$$\hat{p}(\vec{x}_s) = \quad (14)$$

$$i\omega\rho_0 \left\{ \int_S \left[ \frac{\partial G(\vec{x}_s|\vec{x}_S)}{\partial n_S} \left( \int_{(\vec{x}'_S \to \vec{x}_S)} \hat{v}_\eta(\vec{x}_S) d\eta \right) - \hat{v}_\eta(\vec{x}_S) G(\vec{x}_s|\vec{x}_S) \right] dS \right\} \times \left[ 2\pi - \int_S \frac{\partial G(\vec{x}_s|\vec{x}_S)}{\partial n_S} dS \right]^{-1} +$$

$$i\omega\rho_0 \int_{(\vec{x}'_S \to \vec{x}_S)} \hat{v}_\eta(\vec{x}_S) d\eta$$

Substituting Eq. (14) into Eq. (6), we obtain the following integral formulation $$\hat{p}(\vec{x}) = \mathcal{L}_1(\hat{v}_\eta) + \mathcal{L}_2(\hat{v}_n) \quad (15)$$

where $\mathcal{L}_{1,2}$ represent integral operators operating, respectively, on the normal and tangential components of the particle velocity $$\mathcal{L}_1(\hat{v}_\eta) = \frac{i\omega\rho_0}{4\pi} \int_S \left\{ \frac{\partial G(\vec{x}|\vec{x}_S)}{\partial n} \left[ \int_{S'} \frac{\partial G(\vec{x}_S|\vec{x}_{S'})}{\partial n_{S'}} \left( \int_{(\vec{x}'_S \to \vec{x}_S)} \hat{v}_\eta(\vec{x}_S) d\eta \right) dS' \right] \times \left[ 2\pi - \int_{S'} \frac{\partial G(\vec{x}_S|\vec{x}_{S'})}{\partial n_{S'}} dS' \right]^{-1} \right\} dS + \frac{i\omega\rho_0}{4\pi} \int_S \frac{\partial G(\vec{x}|\vec{x}_S)}{\partial n} \left( \int_{(\vec{x}'_S \to \vec{x}_S)} \hat{v}_\eta(\vec{x}_S) d\eta \right) dS \quad (16a)$$

$$\mathcal{L}_2(\hat{v}_\eta) = -\frac{i\omega\rho_0}{4\pi} \int_S \left\{ \frac{\partial G(\vec{x}|\vec{x}_S)}{\partial n} \left[ \int_{S'} \hat{v}_n(\vec{x}_{S'}) G(\vec{x}_S|\vec{x}_{S'}) dS' \right] \times \left[ 2\pi - \int_{S'} \frac{\partial G(\vec{x}_S|\vec{x}_{S'})}{\partial n_{S'}} dS' \right]^{-1} \right\} dS - \frac{i\omega\rho_0}{4\pi} \int_S \hat{v}_n(\vec{x}_S) G(\vec{x}|\vec{x}_S) dS \quad (16b)$$

Equation (15) is the main result of this invention. The radiated acoustic pressure $\hat{p}(\vec{x})$ is shown to be expressible in terms of the particle velocity only. This alternative formulation is in contrast with the classical Kirchhoff integral formulation. There is no need to solve an integral equation for the surface acoustic pressure, given the normal component of the surface velocity. Instead, the radiated acoustic pressure can be calculated directly once the particle velocity at the surface is specified. Since the surface integrals in Eq. (16) can be readily implemented by the standard Gaussian quadratures, the efficiently of numerical computations may be significantly enhanced.

B. Interior Problems

Following the same procedures as outlined above and changing the sign of the unit normal derivative $\partial/\partial n$, we obtain $$\hat{p}(\vec{X}) = \mathcal{L}_1^{int}\{\hat{v}_\eta\} + \mathcal{L}_2^{int}\{\hat{v}_n\} \quad (17)$$

where $\hat{p}(\vec{X})$ represents the acoustic pressure at an interior point $\vec{X}$ enclosed by the surface S, and $\mathcal{L}_{1,2}^{int}$ are defined by $$\mathcal{L}_1^{int}\{\hat{v}_\eta\} = \frac{i\omega\rho_0}{4\pi} \int_S \left\{ \frac{\partial G(\vec{X}|\vec{X}_S)}{\partial n_S} \left[ \int_{S'} \frac{\partial G(\vec{X}_S|\vec{X}_{S'})}{\partial n_{S'}} \left( \int_{(\vec{x}'_s \to \vec{x}_s)} \hat{v}_\eta(\vec{X}_{S'}) d\eta \right) dS' \right] \times \left[ 2\pi + \int_{S'} \frac{\partial G(\vec{X}_S|\vec{X}_{S'})}{\partial n_{S'}} dS' \right]^{-1} \right\} dS - \tag{18a}$$

$$\frac{i\omega\rho_0}{4\pi} \int_S \frac{\partial G(\vec{X}|\vec{X}_S)}{\partial n_S} \left( \int_{(\vec{x}'_s \to \vec{x}_s)} \hat{v}_\eta(\vec{X}_S) d\eta \right) dS$$

$$\mathcal{L}_2^{int}\{\hat{v}_\eta\} = -\frac{i\omega\rho_0}{4\pi} \int_S \left\{ \frac{\partial G(\vec{X}|\vec{X}_S)}{\partial n_S} \left[ \int_{S'} \hat{v}_n(\vec{X}_S) G(\vec{X}_S|\vec{X}_{S'}) dS' \right] \times \left[ 2\pi + \int_{S'} \frac{\partial G(\vec{X}_S|\vec{X}_{S'})}{\partial n_{S'}} dS' \right]^{-1} \right\} dS + \frac{i\omega\rho_0}{4\pi} \int_S \hat{v}_n(\vec{X}_S) G(\vec{X}|\vec{X}_S) dS \tag{18b}$$

C. Scattering problems

In a similar manner, we can extend this alternate formulation to the acoustic pressure field scattered from a finite object in free or half space. For an object in free space, the solution for the scattered acoustic pressure taken the form of $$\hat{p}^{sca}(\vec{x}) = \mathcal{L}_1\{\hat{v}_\eta^{total}\} + \mathcal{L}_2\{\hat{v}_n^{total}\} \tag{19}$$

where $\mathcal{L}_{1,2}$ are defined by Eq. (16), $\hat{v}_\eta^{total}$ and $\hat{v}_n^{total}$ represent the components of the total particle velocity normal and tangential to the surface of the object, respectively, $$\hat{v}_\eta^{total} = (\hat{v}^{sca} + \hat{v}^{inc}) \bullet \vec{e}_\eta \tag{20a}$$

$$\hat{v}_n^{total} = (\hat{v}^{sca} + \hat{v}^{inc}) \bullet \vec{e}_n \tag{20c}$$

where $\hat{v}^{sca}$ and $\hat{v}^{int}$ are the scattered and incident components of the particle velocity, respectively, and $\vec{e}_\eta$ and $\vec{e}_n$ represent the unit vectors in the tangential and normal directions at the surface of the object, respectively.

For an object in half space bounded by an infinite baffle of certain surface acoustic impedance, the effect of the acoustic pressure reflected from the baffle and that scattered from the object due to this reflected wave must all be taken into account. One way of solving the scattered acoustic pressure in the presence of an infinite baffle is to use the image source method. The resulting formulation can be written as $$\hat{p}^{sca}(\vec{x}) = \mathcal{L}_3\{\hat{v}_\eta^{total}\} + \mathcal{L}_4\{\hat{v}_n^{total}\} \tag{21}$$

where $\mathcal{L}_{3,4}$ are given by $$\mathcal{L}_3\{\hat{v}_\eta^{total}\} = \frac{i\omega\rho_0}{4\pi} \int_S \left\{ \frac{\partial G(\vec{x}|\vec{x}_S)}{\partial n_S} \left[ \int_{S'} \frac{\partial G(\vec{x}_S|\vec{x}_{S'})}{\partial n_{S'}} \left( \int_{(\vec{x}'_s \to \vec{x}_s)} \hat{v}_\eta^{total}(\vec{x}_S) d\eta \right) dS' \right] \times \left[ 2\pi - \int_{S'} \frac{\partial G(\vec{x}_S|\vec{x}_{S'})}{\partial n_{S'}} dS' \right]^{-1} \right\} dS + \tag{22a}$$

$$\frac{i\omega\rho_0}{4\pi} \int_S \frac{\partial G(\vec{x}|\vec{x}_S)}{\partial n_S} \left( \int_{(\vec{x}'_s \to \vec{x}_s)} \hat{v}_\eta^{total}(\vec{x}_S) d\eta \right) dS$$

$$\mathcal{L}_4\{\hat{v}_\eta^{total}\} = -\frac{i\omega\rho_0}{4\pi} \int_S \left\{ \frac{\partial G(\vec{x}|\vec{x}_S)}{\partial n_S} \left[ \int_{S'} \hat{v}_n^{total}(\vec{x}_S) G(\vec{x}_S|\vec{x}_{S'}) dS' \right] \times \left[ 2\pi - \int_{S'} \frac{\partial G(\vec{x}_S|\vec{x}_{S'})}{\partial n_{S'}} dS' \right]^{-1} \right\} dS - \frac{i\omega\rho_0}{4\pi} \int_S \hat{v}_n^{total}(\vec{x}_S) G(\vec{x}|\vec{x}_S) dS \tag{22b}$$

where G is the Green's function that accounts for the effect of the image source. For a surface with arbitrary acoustic impedance, there is no closed-form solution for this Green's function. However, for an observer at a point $\vec{x}$ which is at least one half wavelength away from the surface, G can be approximated by $$G(\vec{x}|\vec{x}_S) = \frac{e^{ikR}}{R} + \left( \frac{\cos\theta_I - \beta}{\cos\theta_I + \beta} \right) \frac{e^{ikR_I}}{R_I} \tag{23a}$$

and its normal derivative is given by $$\frac{\partial G(\vec{x}|\vec{x}_S)}{\partial n} = \frac{(ikR - 1)e^{ikR}}{R^2} \frac{\partial R}{\partial n} + \left( \frac{\cos\theta_I - \beta}{\cos\theta_I + \beta} \right) \frac{(ikR_I - 1)e^{ikR_I}}{R_I^2} \frac{\partial R_I}{\partial n} \tag{23b}$$

where R and $R_I$ are the distances measured from the observer to the source and to the image, respectively, $\cos\theta_I = \vec{n}_b \bullet \vec{e}_I$, here $\vec{n}_b$ is the unit normal vector on the baffle and $\vec{e}_I$ is the unit vector in the direction of wave propagation from the image to the observer, $\beta$ is the acoustic admittance of the baffle surface defined by $$\beta = \frac{\rho_0 c}{Z(\omega)} \tag{24}$$

where $Z(\omega)$ is the surface acoustic impedance. For a rigid surface, $Z(\omega) \to \infty$, so $\beta \to 0$ and $G = e^{ikR}/R + e^{ikR_I}/R_I$. On the other hand, for a pressure-release surface, $Z(\omega) \to 0$, so $\beta \to \infty$ and $G = e^{ikR}/R - e^{ikR_I}/R_I$.

III. UNIQUENESS OF SOLUTION

It is well known that in carrying out the numerical computations for the radiated acoustic pressure in the exterior region, the surface Kirchhoff integral equation (8) may fail to yield a unique solution whenever the excitation frequency is close to one of the eigenfrequencies of the interior boundary value problem. This is because Eq. (8) shares the same eigenfrequencies as those of the corresponding integral equation in the interior region, and further, the solution to the adjoint homogeneous equation satisfies the compatibility condition for any velocity distribution $\hat{v}_n(\vec{x})$. Since the alternate formulation (14) is derived from the Kirchhoff integral theory, an examination of its uniqueness seems to be in order. In what follows, we follow the procedures outlined by Schenck to examine the uniqueness of Eq. (14). For brevity, the theorems regarding the characteristic values of an integration kernel, as those regarding trivial and non-trivial solutions to homogeneous and inhomogeneous equations as well as their adjoints are omitted.

The integral formulation governing the acoustic pressure in an interior region is given by $$\hat{p}(\vec{X}) = -\frac{1}{4\pi} \int_S \left[ \frac{\partial G(\vec{X}|\vec{X}_S)}{\partial n_S} \hat{p}(\vec{X}_S) - G(\vec{X}|\vec{X}_S) \frac{\partial \hat{p}(\vec{X}_S)}{\partial n_S} \right] dS \quad (25)$$

Taking a normal derivative of Eq. (25) at an interior point $\vec{X}$ and then lettering $\vec{X} \rightarrow \vec{X}'_S$ from the inside, we obtain $$2\pi \hat{v}_n(\vec{X}'_S) - \int_S \hat{v}_n(\vec{X}_S) \frac{\partial G(\vec{X}'_S|\vec{X}_S)}{\partial n_S} dS = \quad (26)$$

$$-\frac{1}{i\omega \rho_0} \frac{\partial}{\partial n'_S} \int_S \frac{\partial G(\vec{X}'_S|\vec{X}_S)}{\partial n_S} \hat{p}(\vec{X}_S) dS$$

Substituting $\hat{p}(\vec{X}_S)$ on the right side of Eq. (26) by $\vec{p}$ ($\vec{X}'_S$) plus a line integral as given by Eq. (13) yields $$2\pi \hat{v}_n(\vec{X}'_S) - \int_S \hat{v}_n(\vec{X}_S) \frac{\partial G(\vec{X}'_S|\vec{X}_S)}{\partial n_S} dS + \quad (27)$$

$$\frac{\partial}{\partial n'_S} \int_S \frac{\partial G(\vec{X}'_S|\vec{X}_S)}{\partial n_S} \left( \int_{\vec{X}'_S \rightarrow \vec{X}_S} \hat{v}_\eta(\vec{X}_S) d\eta \right) dS =$$

$$-\frac{1}{i\omega \rho_0} \frac{\partial}{\partial n'_S} \int_S \frac{\partial G(\vec{X}'_S|\vec{X}_S)}{\partial n_S} \hat{p}(\vec{X}'_S) dS$$

For the homogeneous Dirichlet problem $\hat{p}(\vec{X}'_S) \equiv 0$. Hence Eq. (27) reduces to $$2\pi \hat{v}_n(\vec{X}'_S) - \int_S \hat{v}_n(\vec{X}_S) \frac{\partial G(\vec{X}'_S|\vec{X}_S)}{\partial n_S} dS + \quad (28)$$

$$\frac{\partial}{\partial n'_S} \int_S \frac{\partial G(\vec{X}'_S|\vec{X}_S)}{\partial n_S} \left( \int_{\vec{X}'_S \rightarrow \vec{X}_S} \hat{v}_\eta(\vec{X}_S) d\eta \right) dS = 0$$

The integral equation governing the surface acoustic pressure in the exterior region is given by Eq. (14). If we consider the homogeneous Neumann problem in which $\hat{v}(\vec{X}_S)$ and take the complex conjugate of this homogeneous equation, we obtain $$\hat{p}\dagger(\vec{X}_S) \left[ 2\pi - \int_S \frac{\partial G(\vec{X}'_S|\vec{X}_S)}{\partial n_S} dS \right] = 0 \quad (29)$$

Obviously, Eq. (29) is different from Eq. (28), so they do not share the same eigenfrequencies. Consequently, Eq. (14) has a unique solution for the radiated acoustic pressure in the exterior region. However, this uniqueness may break down for the special case of a dilating sphere in which and $\hat{v} \equiv \hat{v}_n \vec{e}_n$ and $\hat{v}_\eta \equiv 0$. Since $\hat{v}_n$ is a constant, it can be factored out of the integral sign and Eq. (28) reduces to $$\hat{v}_n \left[ 2\pi - \int_S \frac{\partial G(\vec{X}'_S|\vec{X}_S)}{\partial n_S} dS \right] = 0 \quad (30)$$

which is identical in form to Eq. (29) for the exterior problem. Therefore $\hat{p}\dagger$ and $\hat{v}_n$ share the same eigenfrequencies $\omega^*$.

To check if $\hat{p}\dagger$ also satisfies the compatibility condition given by $$\int_S \hat{p}\dagger(\vec{X}_S) \left[ \int_{S'} \hat{v}_n(\vec{X}_{S'}) G(\vec{X}_{S'}|\vec{X}_S) dS' \right] dS = 0 \quad (31)$$

we return to the integral formulation (25) for the interior region.

Taking the limit as $\vec{X} \rightarrow \vec{X}'_S$ from the inside leads to $$\hat{p}(\vec{X}'_S) \left[ 2\pi + \int_S \frac{\partial G(\vec{X}'_S|\vec{X}_S)}{\partial n_S} dS \right] = \quad (32)$$

$$i\omega \rho_0 \int_S \hat{v}_n(\vec{X}_S) G(\vec{X}'_S|\vec{X}_S) dS -$$

$$i\omega \rho_0 \int_S \frac{\partial G(\vec{X}'_S|\vec{X}_S)}{\partial n_S} \left( \int_{\vec{X}'_S \rightarrow \vec{X}_S} \hat{v}_\eta(\vec{X}_S) d\eta \right) dS$$

Since $\hat{v}_\eta(\vec{X}_S) = 0$, the second term on the right side of Eq. (32) vanishes identically. Therefore, for the interior homogeneous Dirichlet problem for which $\hat{p}(\vec{X}_S) \equiv 0$ and $\omega = \omega^*$ we have $$\int_S \hat{v}_n(\vec{X}_S) G(\vec{X}'_S|\vec{X}_S) dS = 0 \quad (33)$$

Because of the equivalence of $\hat{v}_n(\vec{X}_S)$ and $\hat{p}\dagger(\vec{X}_S)$, we can rewrite Eq. (33) as $$\int_S \hat{p}\dagger(\vec{X}_S) G(\vec{X}'_S|\vec{X}_S) dS = 0 \quad (34)$$

Interchanging the order of integrations in Eq. (31) yields $$\int_{S'} \hat{v}_n(\vec{X}_{S'}) \left[ \int_S \hat{p}\dagger(\vec{X}_S) G(\vec{X}_S|\vec{X}_{S'}) dS \right] dS' = 0 \quad (35)$$

Since the square-bracket term in Eq. (35) is identically zero [see Eq. (34)], the compatibility condition (31) is satisfied. Consequently, for a dilating sphere Eq. (14) may fail to yield a unique solution for the surface acoustic pressure whenever the excitation frequency is close to one of the corresponding interior Dirichlet eigenfrequencies. However, the ill-conditioning in the numerical computation of Eq. (14) is much less severe than that in the BEM-based Kirchhoff integral equation, as shown below.

For a dilating sphere, the solution for the surface acoustic pressure given by Eq. (14) takes the following form $$\hat{p} = -i\omega \rho_0 \hat{v}_n \int_S \frac{e^{ikR_S}}{R_S} dS \times \quad (36)$$

$$\left[ 2\pi - \int_{S'} \frac{(ikR_{S'} - 1)e^{ikR_{S'}}}{R_{S'}^2} \frac{\partial R_{S'}}{\partial n_{S'}} dS' \right]^{-1}$$

The corresponding interior Dirichlet eigenfrequencies are determined by the roots of the first kind of the spherical Bessel function of order zero, $T_o(k^*a) = 0$, which yields $k^*a = m\pi$, where m is an integer and a is the radius of the sphere. Using the spherical coordinates, it is easy to show that $R_S=2a\cos(\theta/2)$, $\partial R_S/\partial n_S=\cos(\theta/2)$, and $dS=a^2\sin\theta d\theta d\phi$, where $\theta$ and $\phi$ vary from 0 to $\pi$ and 0 to $2\pi$, respectively.

Substituting $R_S$, $\partial R_S/\partial n_S$, and $dS$ into Eq. (36), we obtain $$\hat{p} = \frac{i\rho_0 c \hat{v}_n ka}{(1-ika)} \times \frac{(1-e^{i2ka})}{(1-e^{i2ka})} \tag{37}$$

When $ka=m\pi$, Eq. (37) reduces to $\hat{p}=-iv_0 c\hat{\rho}_n m\pi(1-m\pi)^{-1}\times(0/0)$. However, the computer cannot take the limit to (0/0). Hence any round-off error in the numerical computation may lead to an erroneous result.

In using the BEM-based Kirchhoff integral equation, the surface acoustic pressure is obtained by solving a set of simultaneous integral equations. When the excitation frequency is close to one of the interior eigenfrequencies, the diagonal terms become very small and the matrix becomes ill-conditioned. Table 1 exhibits this trend in detail for a dilating sphere around $ka=\pi$ and $2\pi$. Here numerical computations are carried out by a general BEM code with the spherical surface discretized into 48 quadratic quadrilaterals and 130 nodes. The results thus obtained are compared with those of Eq. (14).

With Eq. (14) one can carry out surface integrals using Gaussian quadratures directly, without the need of solving a set of simultaneous equations. In evaluating these integrations, we make use of the axisymmetry of the acoustic pressure distribution and discretize the spherical surface into twelve rings along the generator. The integrations with respect to the polar angle $\theta$ within each ring are carried out by the Gaussian quadrature formula with three interior points. The integration over the azimuthal angle $\rho$ can be done independently, yielding a factor of $2\pi$.

Numerical results in Table 1 show that both BEM and Eq. (14) fail to yield unique solutions at the interior Dirichlet eigenfrequencies. However, the BEM results show the sign of ill-conditioning over a large frequency range around the interior Dirichlet eigenfrequencies, whereas the results obtained by Eq. (14) are more or less correct until ka hits the eigenfrequencies almost directly.

As a second example, we calculate the dimensionless acoustic pressures on the surface of an oscillating sphere. The corresponding interior eigenfrequencies are determined by the roots of the first kind of the spherical Bessel function of order one, $T_1(k^*a)=0$, which yields $k^*a=4.493409, 7.725233, \ldots$. Since in this case the tangential component of the particle velocity is not zero and the normal component of the velocity is not constant, the complex conjugate of the homogeneous equation (29) for the exterior region does not share the same eigenfrequencies as those of the homogeneous equation (28) for the interior problem. Hence, the solution given by Eq. (14) is unique, while those obtained by the BEM-based Kirchhoff integral formulation are not as $ka \to k^*a$.

Table 2 lists the dimensionless acoustic pressures obtained by BEM and Eq. (14), respectively, on the surface of an oscillating sphere at $\theta=45°$. In using Eq. (14) we divide the spherical surface into eighteen rings along its generator in order to compare the surface acoustic pressure at the same location as those of BEM with 130 nodes. Numerical results demonstrate that the BEM results show the sign of ill-conditioning over a large frequency range around the interior eigenfrequencies, whereas the results of Eq. (14) are accurate and unique.

In the last example, we use Eq. (14) to calculate the acoustic pressure on the surface of a right cylinder of finite length. The aspect ratio of the cylinder is b/a=1, where a and b are the radius and half length of the cylindrical wall, respectively. The eigenfrequencies of the corresponding boundary value problem in the interior region are give by $$k^*_{mnq} = \sqrt{\left(\frac{m\pi}{2b}\right)^2 + \left(\frac{\alpha_{nq}}{a}\right)^2} \tag{38}$$

where m is a positive integer and $\alpha_{nq}$ is the qth root of the nth Bessel function $$J_n(\alpha_{nq})=0 \quad n=0,1,2, \tag{39}$$

Thus, for a=b=1 (m) the first two eigenfrequencies are $k^*_{101}a=2.8724 \ldots$ and $k^*_{210}a=3.9563 \ldots$.

In the following, we examine the uniqueness of the numerical solutions given by Eq. (14) around ka=2.8724 and 3.9563, respectively. Since there exists no analytical solution for a finite cylinder, comparisons of the numerical result of Eq. (14) are made with respect to the radiated acoustic pressures from a point source of radius $a_o$ ($a_o$=0.001a) located at the center of the cylinder. The procedures are described as follows. First, we calculate the acoustic pressure distribution on a cylindrical surface due to a point source. Next, we determine the particle velocity $\vec{v}^*(\vec{x}_S)$ on the cylindrical surface via Eq. (9). Once $\vec{v}^*(\vec{x}_S)$ is specified, the surface acoustic pressure is recalculated using Eq. (14). The results thus obtained are compared with the surface acoustic pressure due to the point source.

In carrying out the numerical integrations in Eq. (14), we uniformly divide the surface into 48 rings along its generator, i.e., 12 rings on each of the two flat ends and 24 rings on the side wall. Each of these 48 rings is further divided into 48 equal segments along the circumference. Numerical integrations over each segment are carried out by Gaussian quadratures with nine interior points. Table 3 lists the maximum relative errors of the magnitudes and phases of the dimensionless surface acoustic pressures given by Eq. (14) as compared with those from a point source around ka=2.8724 and 3.9563. It is seen that Eq. (14) shows no signs of the nonuniqueness difficulties around these characteristic frequencies. The relative error in the magnitude of the dimensionless surface acoustic pressure increases monotonically with ka, which is to be expected for a fixed grid size. The relative error in the phase of the surface acoustic pressure remains essentially the same however.

Figure 3:
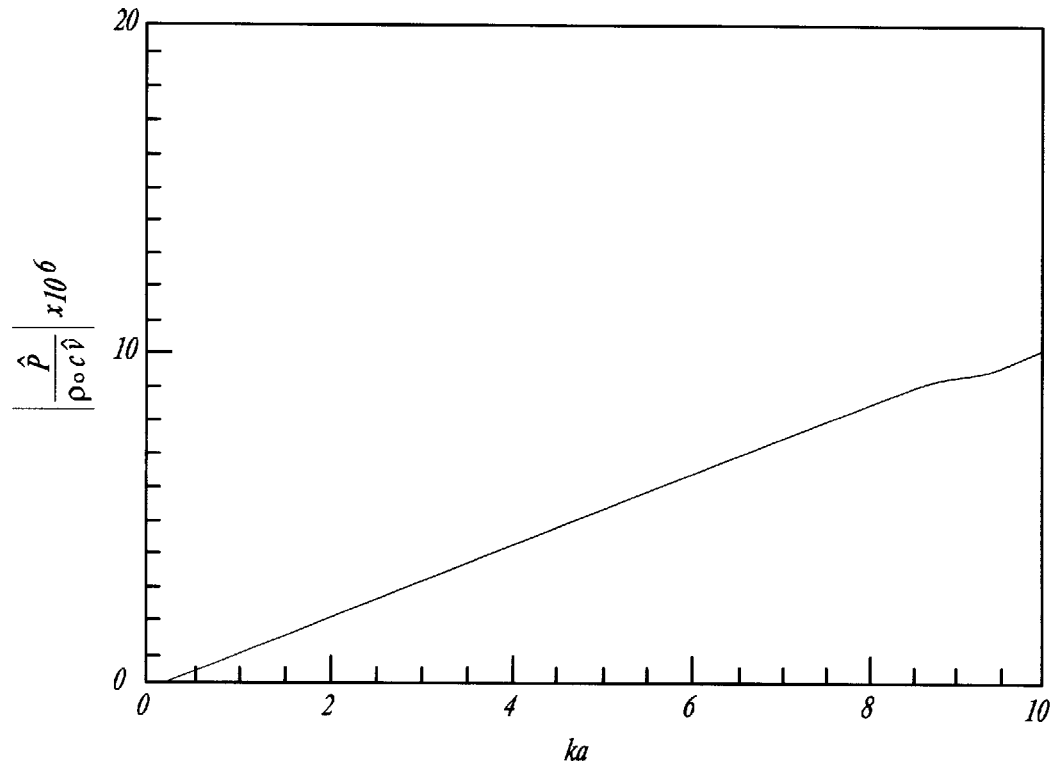
FIG. 3 shows the uniqueness of solution obtained by using Eq. (14) for dimensionless surface acoustic pressure for a finite cylinder.

FIG. 3 displays the magnitude of the dimensionless surface acoustic pressure evaluated at the center of a flat end of the cylinder using Eq. (14) with ka varying from 0 to 10 at an increment at $\Delta ka=0.1$. Within this frequency range, there could be many characteristic frequencies for the corresponding interior boundary value problem [see Eq. (39)]. Nevertheless, the numerical solution given by Eq. (14) is always unique.

In summary, solutions given by Eq. (14) are unique, except for the special case of a dilating sphere. Even under this circumstance, the ill-conditioning in the numerical computation is much less severe than that of the BEM-based Kirchhoff integral formulation.

TABLE 1

Dimensionless acoustic pressures on the surface of a dilating sphere around $ka = \pi$ and $2\pi$.

| ka | Exact values | BEM | Errors (%) | Eq. (14) | Errors (%) |
|---|---|---|---|---|---|
| 2.0 | 8.94427E−01 | 8.39306E−01 | 6.16 | 8.94427E−01 | <0.01 |
| 3.0 | 9.48683E−01 | 4.73109E−01 | 50.13 | 9.48682E−01 | <0.01 |
| 3.14 | 9.52846E−01 | 3.86143E+01 | 3,952.52 | 9.52724E−01 | 0.01 |
| 3.1415 | 9.52888E−01 | 1.89415E+02 | 19,777.99 | 9.51050E−01 | 0.14 |
| 3.141592 | 9.52890E−01 | 8.62446E+01 | 8,950.85 | 6.68342E−01 | 29.82 |
| 3.1416 | 9.52891E−01 | 6.57239E+01 | 6,797.32 | 9.78423E−01 | 2.68 |
| 3.15 | 9.53124E−01 | 8.96201E+00 | 840.28 | 9.53145E−01 | <0.01 |
| 4.0 | 9.70142E−01 | 1.02209E+00 | 5.35 | 9.70143E−01 | <0.01 |
| 5.0 | 9.80581E−01 | 9.26171E−01 | 5.55 | 9.80582E−01 | <0.01 |
| 6.0 | 9.86394E−01 | 5.10893E−01 | 48.21 | 9.86401E−01 | <0.01 |
| 6.28 | 9.87558E−01 | 4.38667E+01 | 4,341.94 | 9.87923E−01 | 0.04 |
| 6.2830 | 9.87570E−01 | 1.33935E+02 | 13,462.08 | 9.94231E−01 | 0.67 |
| 6.283185 | 9.87571E−01 | 1.36584E+02 | 13,730.30 | 3.57967E+00 | 262.47 |
| 6.2832 | 9.87571E−01 | 1.51351E+02 | 15,225.58 | 9.94820E−01 | 0.73 |
| 6.30 | 9.87636E−01 | 1.01460E+01 | 927.30 | 9.87578E−01 | <0.01 |
| 7.0 | 9.89950E−01 | 1.08205E−00 | 9.30 | 9.89959E−01 | <0.01 |
| 8.0 | 9.92278E−01 | 5.34767E−01 | 46.11 | 9.92307E−01 | <0.01 |
| 9.0 | 9.93884E−01 | 2.20737E−01 | 77.79 | 9.93971E−01 | <0.01 |

TABLE 2

Dimensionless acoustic pressures on the surface of an oscillating sphere at $\theta = 45°$ around $ka = 4.493409$ and $7.725233$.

| ka | Exact values | BEM | Errors (%) | Eq. (14) | Errors (%) |
|---|---|---|---|---|---|
| 2.0 | 7.07107E−01 | 7.13086E−01 | 0.85 | 7.04691E−01 | 0.34 |
| 3.0 | 7.27607E−01 | 7.06985E−01 | 2.83 | 7.12135E−01 | 2.13 |
| 4.0 | 7.23240E−01 | 5.91681E−01 | 18.19 | 7.25003E−01 | 0.24 |
| 4.49 | 7.20893E−01 | 1.91477E+01 | 2,556.11 | 7.21653E−01 | 0.11 |
| 4.4934 | 7.20878E−01 | 3.20628E+01 | 4,347.74 | 7.21633E−01 | 0.10 |
| 4.493409 | 7.20878E−01 | 3.10966E+01 | 4,213.71 | 7.21633E−01 | 0.10 |
| 4.4935 | 7.20877E−01 | 3.07347E+01 | 4,163.53 | 7.21632E−01 | 0.10 |
| 4.5 | 7.20848E−01 | 1.01860E+01 | 1,313.06 | 7.21594E−01 | 0.10 |
| 5.0 | 7.18814E−01 | 8.43812E−01 | 17.39 | 7.18925E−01 | 0.02 |
| 6.0 | 7.15757E−01 | 7.20351E−01 | 0.64 | 7.12663E−01 | 0.43 |
| 7.0 | 7.13691E−01 | 2.93555E−01 | 58.87 | 7.15355E−01 | 0.23 |
| 7.72 | 7.12613E−01 | 2.57310E+01 | 3,510.80 | 7.13362E−01 | 0.11 |
| 7.7252 | 7.12606E−01 | 1.26346E+02 | 17,630.13 | 7.13351E−01 | 0.10 |
| 7.725233 | 7.12606E−01 | 1.34069E+02 | 18,713.90 | 7.13350E−01 | 0.10 |
| 7.7253 | 7.12606E−01 | 1.15068E+02 | 16,047.49 | 7.13350E−01 | 0.10 |
| 7.73 | 7.12600E−01 | 2.61664E+01 | 3,571.96 | 7.13340E−01 | 0.10 |
| 8.0 | 7.12262E−01 | 1.21748E+00 | 70.93 | 7.12789E−01 | 0.07 |
| 9.0 | 7.11241E−01 | 9.11500E−01 | 28.16 | 7.10350E−01 | 0.13 |

TABLE 3

Maximum relative errors of the magnitudes and phases of the dimensionless acoustic pressures on the surface of a finite cylinder by using Eq. (14) around $ka$ 2.8724 and 3.9563.

| ka | Exact Mag. | Eq. (14) | Errors (%) | Exact Phase | Eq (14) | Errors (%) |
|---|---|---|---|---|---|---|
| 1.5 | 0.1083E−05 | 0.1083E−05 | 0.035 | 29.04 | 29.02 | 0.056 |
| 2.0 | 0.1759E−05 | 0.1760E−05 | 0.057 | 40.32 | 40.34 | 0.043 |
| 2.5 | 0.2498E−05 | 0.2502E−05 | 0.158 | 53.36 | 53.44 | 0.145 |
| 2.8 | 0.2798E−05 | 0.2806E−05 | 0.288 | 70.57 | 70.62 | 0.077 |
| 2.87 | 0.2868E−05 | 0.2877E−05 | 0.331 | 74.58 | 74.63 | 0.061 |
| 2.872 | 0.2869E−05 | 0.2879E−05 | 0.332 | 74.70 | 74.74 | 0.061 |
| 2.8723 | 0.2870E−05 | 0.2879E−05 | 0.332 | &4.71 | 74.76 | 0.061 |
| 2.8724 | 0.2870E−05 | 0.2879E−05 | 0.332 | 74.72 | 74.76 | 0.061 |
| 2.873 | 0.2870E−05 | 0.2880E−05 | 0.333 | 74.75 | 74.80 | 0.060 |
| 2.88 | 0.2877E−05 | 0.2887E−05 | 0.337 | 75.16 | 75.20 | 0.059 |
| 2.9 | 0.2897E−05 | 0.2908E−05 | 0.351 | 76.30 | 76.34 | 0.054 |
| 3.0 | 0.2997E−05 | 0.3010E−05 | 0.427 | 82.04 | 72.06 | 0.030 |
| 3.5 | 0.3497E−05 | 0.3534E−05 | 1.053 | 110.71 | 110.63 | 0.073 |
| 3.9 | 0.3897E−05 | 0.3951E−05 | 1.397 | 133.65 | 133.64 | 0.005 |
| 3.95 | 0.3947E−05 | 0.4001E−05 | 1.384 | 136.51 | 136.53 | 0.011 |

TABLE 3-continued

Maximum relative errors of the magnitudes and phases of the dimensionless acoustic pressures on the surface of a finite cylinder by using Eq. (14) around ka 2.8724 and 3.9563.

| ka | Exact Mag. | Eq. (14) | Errors (%) | Exact Phase | Eq (14) | Errors (%) |
|---|---|---|---|---|---|---|
| 3.956 | 0.3953E–05 | 0.4007E–05 | 1.381 | 136.86 | 136.86 | 0.013 |
| 3.9563 | 0.3953E–05 | 0.4007E–05 | 1.381 | 136.88 | 136.89 | 0.013 |
| 3.9564 | 0.3953E–05 | 0.4008E–05 | 1.381 | 136.88 | 136.90 | 0.014 |
| 3.957 | 0.3954E–05 | 0.4008E–05 | 1.381 | 136.92 | 136.93 | 0.014 |
| 3.96 | 0.3957E–05 | 0.4011E–05 | 1.380 | 137.09 | 137.11 | 0.015 |
| 4.0 | 0.3997E–05 | 0.4051E–05 | 1.359 | 139.38 | 139.42 | 0.028 |

IV. ANALYTIC VALIDATIONS

In this section, we demonstrate the validations of the alternate formulation derived in this invention on sound radiation from vibrating spheres whose analytic solutions are well-known.

A. A dilating sphere

In the first example, we consider acoustic radiation from a sphere of radius a vibrating radially at a constant frequency $\omega$ in a free field. Since the sphere dilates uniformly in all direction, the particle velocity $\hat{v} = \hat{v}_n \vec{e}$, where $\hat{v}_n$ is a constant. Substituting $\hat{v}_n$ into (15) yields $$\hat{p}(\vec{x}) = -\frac{i\omega\rho_0 \hat{v}_n}{4\pi} \int_S \left\{ \frac{(ikR-1)e^{ikR}}{R^2} \frac{\partial R}{\partial n} \times \left[ \int_{S'} \frac{e^{ikR_{S'}}}{R_{S'}} dS' \right] \times \left[ 2\pi - \int_{S'} \frac{(ikR_{S'}-1)e^{ikR_{S'}}}{R_{S'}^2} \frac{\partial R_{S'}}{\partial n_{S'}} dS' \right]^{-1} \right\} dS - \frac{i\omega\rho_0 \hat{v}_n}{4\pi} \int_S \frac{e^{ikR}}{R} dS \quad (40)$$

The surface integrals in the square brackets on the right side of Eq. (40) can be evaluated independently and the results are $$\left[ \int_{S'} \frac{e^{ikR_{S'}}}{R_{S'}} dS' \right] = \frac{i2\pi}{k}(1 - e^{i2ka}) \quad (41a \text{ and } 41b)$$

$$\left[ 2\pi - \int_{S'} \frac{(ikR_{S'}-1)e^{ikR_{S'}}}{R_{S'}^2} \frac{\partial R_{S'}}{\partial n_{S'}} dS' \right] = \frac{i2\pi}{ka}(1 - ika)(1 - e^{i2ka})$$

Substituting Eq. (41) into (40) leads to $$\hat{p}(\vec{x}) = \frac{i\omega\rho_0 \hat{v}_n}{4\pi} \int_0^{2\pi} \int_0^{\pi} \left[ \left( \frac{a}{1-ika} \right) \frac{(1-ikR)}{R} \frac{\partial R}{\partial n} - 1 \right] \frac{e^{ikR}}{R} a^2 \sin\theta_S d\theta_S d\phi_S \quad (42)$$

where $$R = \sqrt{r^2 + a^2 - 2ar(\sin\theta\cos\phi\sin\theta_S\cos\phi_S + \sin\theta\sin\phi\sin\theta_S\sin\phi_S + \cos\theta\cos\theta_S)} \quad (43a)$$

$$\frac{\partial R}{\partial n} = -R^{-1}[(r\sin\theta\cos\phi - a\sin\theta_S\cos\phi_S)\sin\theta_S\cos\phi_S + (r\sin\theta\sin\phi - a\sin\theta_S\sin\phi_S)\sin\theta_S\sin\phi_S + (r\cos\theta - a\cos\theta_S)\cos\theta_S] \quad (43b)$$

where r is the distance from the center of the sphere to the observation point in the filed, $\theta$ and $\phi$ are the polar and azimuthal angles of the field point, and $\theta_S$ and $\phi_S$ are the polar and azimuthal angles of a surface point.

Since the radiated acoustic pressure is spherically symmetric, we can set the field point to lie on any axis, say, $\theta = \pi$ and $\phi = 0$. Thus, R and $\partial R/\partial n$ can be simplified to $$R = \sqrt{r^2 + a^2 + 2ar\cos\theta_S} \quad (44)$$

and $$\frac{\partial R}{\partial n} = \frac{a + r\cos\theta_S}{\sqrt{r^2 + a^2 + 2ar\cos\theta_S}}$$

Substituting Eq. (44) into (42), we obtain $$\hat{p}(\vec{x}) = -\frac{\rho_0 c \hat{v}_n a}{2r} \left\{ \frac{(1+ika)e^{ik(r-a)} - (1-ika)e^{ik(r+a)}}{(1-ika)} - [e^{ik(r-a)} - e^{ik(r+a)}] \right\} \quad (45)$$

$$= -\frac{i\rho_0 c \hat{v}_n ka}{(1-ika)} \left( \frac{a}{r} \right) e^{ik(r-a)}$$

which agrees exactly with the analytic solution.

B. An oscillating sphere

The second example concerns sound radiation from a sphere oscillating back and forth along the z axis at a constant frequency, $\omega$ in an unbounded fluid medium. To check the validity of the alternate formulation, we substitute the analytic solution for the particle velocity $$\hat{v}_n(\vec{x}_S) = \hat{v}_c \cos\theta \qquad \hat{v}_\theta(\theta) = \frac{\hat{v}_c(1-ika)\sin\theta}{(2 - k^2 a^2 - i2ka)} \quad (46)$$

into the alternate formulation and then compare the resulting acoustic pressure with that of the analytic solution. In Eq. (46), $\theta$ is the angle between the unit outward normal and the z-axis direction, $\vec{v}_c$ is the magnitude of the velocity at the center of the sphere.

Because of the presence of $\hat{v}_\theta$, evaluation of the integrals in Eq. (15) become a bit lengthy. Without loss of generality, we demonstrate the evaluation of the surface acoustic pressure given by Eq. (14). To this end, we first carry out the line integral involved in Eq. (14). Using the axisymmetry, we can set $\vec{x}'_s$ at $(a, \pi, 0)$ and $\vec{x}_s$ at $(a, \theta, \phi)$. Substituting Eq. (46) into the line integral on the right side of Eq. (14) then yields $$\int_\pi^\theta \hat{v}_\theta(\theta')ad\theta' = \int_\pi^\theta \frac{\hat{v}_c(1-ika)\sin\theta'}{(2-k^2a^2-i2ka)} ad\theta' = \tag{47}$$

$$-\frac{a\hat{v}_c(1-ika)(1+\cos\theta)}{(2-k^2a^2-i2ka)}$$

Substituting Eqs. (41) and (47) into (14) leads to $$\begin{aligned}
\hat{p}(\vec{x}_s) &= -\frac{\rho_0 c\hat{v}_c(k^2a)}{2\pi(1-ika)(1-e^{i2ka})} \times \int_S \left[ \frac{a(1-ika)}{(2-k^2a^2-i2ka)} \frac{(1+\cos\theta)(ikR_S-1)}{R_S} \frac{\partial R_S}{\partial n_S} + \cos\theta \right] \frac{e^{ikR_S}}{R_S} dS - \\
&\quad \frac{i\rho_0 c\hat{v}_c ka(1-ika)(1+\cos\theta)}{(2-k^2a^2-i2ka)} \\
&= -\frac{i\rho_0 c\hat{v}_c}{ka(1-ika)(1-e^{i2ka})} \left\{ \frac{(1-ika)[2 - e^{i2ka}(i2K^3a^3 - 4k^2a^2 - i4ka + 2)]}{(2-k^2a^2-i2ka)} - [1 + k^2a^2 + e^{i2ka}(k^2a^2 + i2ka - 1)] \right\} - \\
&\quad \frac{i\rho_0 c\hat{v}_c ka(1-ika)(1+\cos\theta)}{(2-k^2a^2-i2ka)} \\
&= \frac{i\rho_0 c\hat{v}_c ka(1-k^2a^2-i2ka)}{(1-ika)(2-k^2a^2-i2ka)} - \frac{i\rho_0 c\hat{v}_c ka(1-ika)(1+\cos\theta)}{(2-k^2a^2-i2ka)} \\
&= \frac{i\rho_0 c\hat{v}_c ka(1-ika)\cos\theta}{(2-k^2a^2-i2ka)}
\end{aligned} \tag{48}$$

which agrees perfectly with the analytic solution.

C. A partially vibrating sphere

The third example deals with acoustic radiation from a sphere on which only part of the surface is vibrating at a constant frequency ω As before, we substitute the analytical solution for the particle velocity into Eqs. (14) and (15), and then compare the acoustic pressures thus obtained with the known values. For simplicity, we assume that the particle velocity is axisymmetric, and that the normal component of the particle velocity is equal to that of the surface velocity, which is limited to the portion described by the half-vertex angle $\theta_o$ $$\hat{v}_n(\theta) = \hat{v}_o H(\theta_o - \theta) \qquad 0 \leq \theta \leq \pi \tag{49a}$$

$$\hat{v}_\theta(\theta) = \frac{\hat{v}_o}{i2ka} \sum_{m=0}^\infty [P_m - 1(\cos\theta_0) - P_{m+1}(\cos\theta_0)] \frac{h_m(ka)}{B_m(ka)e^{i\delta_m(ka)}} \frac{dP_m(\cos\theta)}{d\theta} \tag{49b}$$

where $H(\theta_o - \theta)$ is the Heaviside step function, which is unity when $\theta \leq \theta_o$ and zero when $\theta > \theta_o$, $\hat{v}_o$ is the magnitude of the surface velocity, $P_m$ and $h_m$ represent the Legendre and the spherical Hankel functions of order m, respectively, and $B_m$ and $\delta_m$ stand for the amplitudes and phase angles of acoustic radiation of order m, respectively.

Substituting Eq. (49) into (14) and (15), we obtain $$\hat{p}(\vec{x}_S) = \frac{\rho_0 c(ka)^2}{2\pi(1-ika)(1-e^{i2ka})} \times \int_S \left[ \frac{\partial R_S}{\partial n_S} \frac{(ikR_S-1)e^{ikR_S}}{R_S^2} \left( \int_\pi^\theta \hat{v}_\theta(\theta')d\theta' \right) - \frac{\hat{v}_n(\theta)e^{ikR_S}}{aR_S} \right] dS + i\rho_0 c(ka) \int_\pi^\theta \hat{v}_\theta(\theta')d\theta' \tag{50a}$$

$$\hat{p}(\vec{x}) = \frac{\rho_0 c(ka)^2}{8\pi^2(1-ika)(1-e^{i2ka})} \times \int_S \frac{(ikR_S-1)e^{ikR}}{R^2} \frac{\partial R}{\partial n} \left[ \int_{S'} \frac{(ikR_{S'}-1)e^{ikR_{S'}}}{R_{S'}^2} \frac{\partial R_{S'}}{\partial n_{S'}} \left( \int_\pi^\theta \hat{v}_\theta(\theta')d\theta' \right) dS' \right] dS + \tag{50b}$$

$$\frac{i\rho_0 c(ka)}{4\pi} \int_S \frac{(ikR-1)e^{ikR}}{R^2} \frac{\partial R}{\partial n} \left( \int_\pi^\theta \hat{v}_\theta(\theta')d\theta' \right) dS + \frac{\rho_0 c(k^2a)}{8\pi^2(1-ika)(1-e^{i2ka})} \int_S \frac{(ikR-1)e^{ikR}}{R^2} \frac{\partial R}{\partial n} \left[ \int_{S'} \frac{\hat{v}_n(\theta)e^{ikR_{S'}}}{R_{S'}} dS' \right] dS - $$

$$\frac{i\omega\rho_0}{4\pi} \int_S \frac{\hat{v}_n(\theta)e^{ikR}}{R} dS$$

Once again, we use the axisymmetry of the acoustic pressure distribution to set $\phi=0$ and replace R and $\partial R/\partial n$ in Eq. (50), respectively, by $$R + \sqrt{r^2 + a^2 - 2ar(\sin\theta\sin\theta_S\cos\phi_S + \cos\theta\cos\theta_S)} \quad (51c)$$

$$\frac{\partial R}{\partial n} = \frac{a - r(\sin\theta\sin\theta_S\cos\phi_S + \cos\theta\cos\theta_S)}{R} \quad (51b)$$

In this case, however, an exact solution cannot be found. Hence $\hat{p}(\vec{x}_S)$ and $\hat{p}(\vec{x})$ are solved numerically. Here, we the radius and half length of the cylindrical wall, respectively. Since there are no analytic solutions available, we compare the acoustic pressures given by Eqs. (14) and (15) with those of a monopole and a dipole sources, respectively, located at the center of the cylinder. The radii of the monopole and the dipole are $a_0 = 0.001a$, where $a = 1(m)$. The procedures involved in these comparisons are the same as those described in Section III.

TABLE 4

Dimensionless acoustic pressure on the surface of a partially vibrating sphere with $\theta_0 = 45°$ and ka = 0.1.

| θ | $|\hat{p}/\rho_0 c \hat{v}_0|$ | Eq. (50a) | Errors | Phase | Eq. (50a) | Errors |
|---|---|---|---|---|---|---|
| 7.5° | 5.1455E−02 | 5.0672E−02 | 1.52% | −88.375° | −88.350° | 0.03% |
| 37.5° | 4.0547E−02 | 3.7969E−02 | 6.36% | −87.940° | −87.800° | 0.16% |
| 67.5° | 1.3494E−02 | 1.3280E−02 | 1.59% | −83.816° | −83.716° | 0.12% |
| 97.5° | 7.7016E−03 | 7.8862E−03 | 2.40% | −79.158° | −79.414° | 0.32% |
| 127.5° | 5.7574E−03 | 5.6945E−03 | 1.09% | −75.472° | −75.308° | 0.22% |
| 157.5° | 5.0335E−03 | 4.9149E−03 | 2.36% | −73.361° | −72.948° | 0.56% |
| 172.5° | 4.8551E−03 | 4.7616E−03 | 1.93% | −72.738° | −72.388° | 0.48% |

TABLE 5

Dimensionless acoustic pressures evaluated at kr = 1 from a partially vibrating sphere with $\theta_0 = 45°$ and ka = 0.1.

| θ | $|\hat{p}/\rho_0 c \hat{v}_0|$ | Eq. (50a) | Errors | Phase | Eq. (50a) | Errors |
|---|---|---|---|---|---|---|
| 0° | 1.5576E−03 | 1.6646E−03 | 0.17% | −39.712° | −39.436° | 0.70% |
| 45° | 1.5980E−03 | 1.5959E−03 | 0.13% | −37.607° | −37.357° | 0.66% |
| 90° | 1.4523E−03 | 1.4542E−03 | 0.13% | −32.433° | −32.381° | 0.16% |
| 135° | 1.3333E−03 | 1.3404E−03 | 0.53% | −27.184° | −27.523° | 1.25% |
| 180° | 1.2907E−03 | 1.2998E−03 | 0.71% | −25.001° | −25.556° | 2.22% | discretize the spherical surface into twelve rings along θ and twenty-four segments along φ within each ring. Numerical integrations over each segment are carried out using Gaussian quadratures with none interior points. For convenience, we set ka=0.1, kr=1, $\theta_0=45°$, and use sixteen expansion terms in Eq. (49b) to approximate the tangential component of the particle velocity $\hat{v}_\theta$. Table 4 compares the numerical results of Eq. (50a) at various polar angles θ with the analytic solutions. The maximum relative error in the magnitude of the surface acoustic pressure is found to be about six percent, while that in the corresponding phase angles is less than one percent. The magnitudes of the relative errors decay rapidly as the measurement point moves into the field. Table 5 shows the comparison of the numerical result of Eq. (50b) at the same polar angles at kr=1 with the analytic solution. In this case, the maximum relative error in the magnitude of the Field acoustic pressure is less than one percent.

V. NUMERICAL VALIDATIONS

In the preceding section, we demonstrate validations of the alternate formulation on sound radiation from vibrating objects whose analytic solutions are well-known. In this section, we consider cases for which there exist no analytic solutions.

In order for the vibrating objects to be of certain generality, we choose a slender cylinder with two flat ends. The aspect ratio of the cylinder is b/a=10, where a and b are In what follows, we first consider the case in which the particle velocity field on the cylindrical surface is generated by a monopole located at the center of the cylinder. Substituting the velocity field into Eqs. (14) and (15) yields the surface and field acoustic pressures, which are then compared with those from the monopole source, respectively. Excellent agreements are obtained for all the cases tested. For brevity, however, we only plot the comparisons of kb=1 and 50 below. The surface integrals in Eqs. (14) and (15) are implemented with the cylindrical surface discretized into 480 rings on the side wall and 24 rings on each end. These rings are further discretized into 48 segments along the azimuth. Numerical integrations over each segment are carried out using Gaussian quadratures with nine interior points.

Figure 4A:
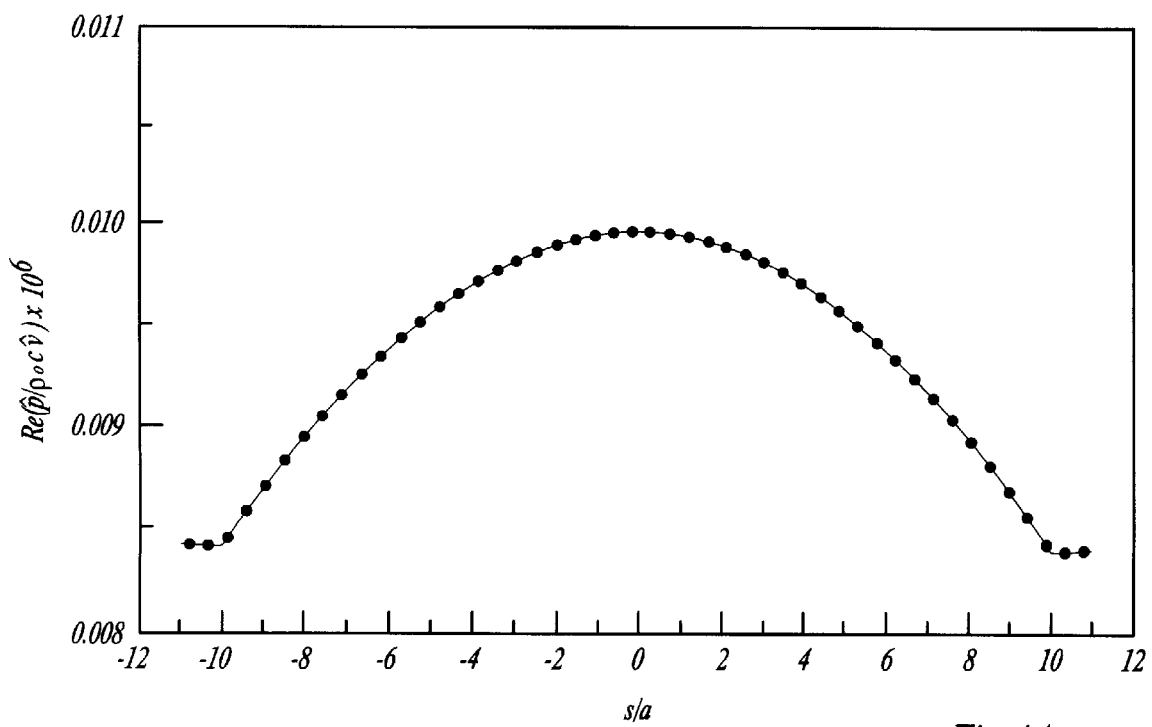
FIG. 4a is a comparison of the dimensionless acoustic pressure given by Eq. (14), real part, and the exact solution.
Figure 4B:
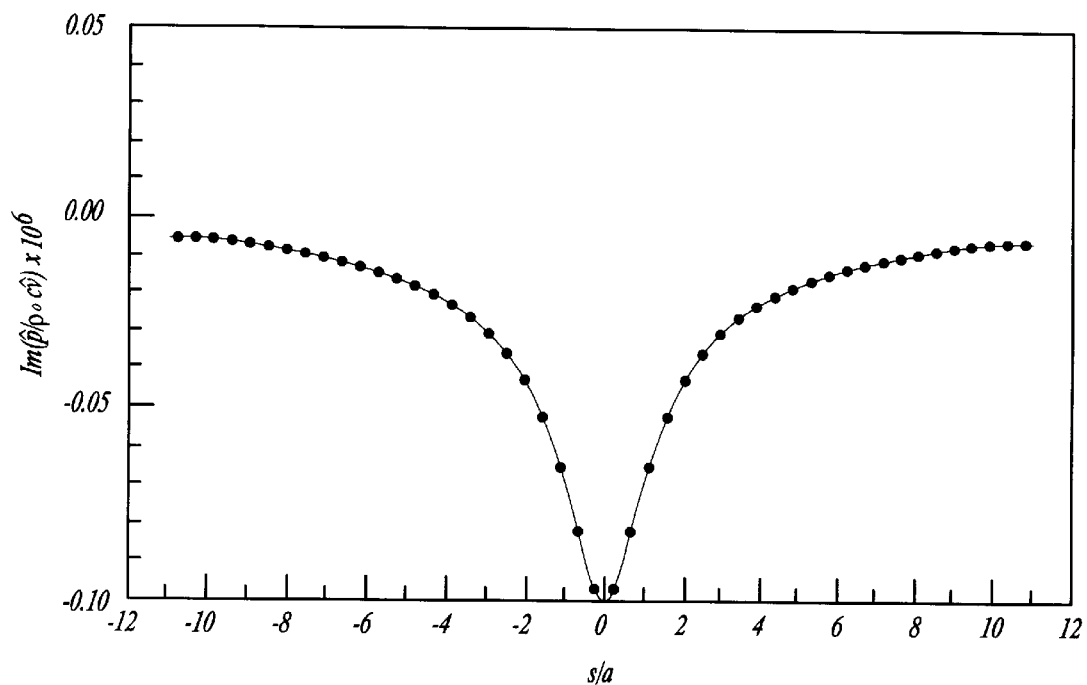
FIG. 4b is a comparison of the dimensionless acoustic pressure given by Eq. (14), imaginary part, and the exact solution.
Figure 5:
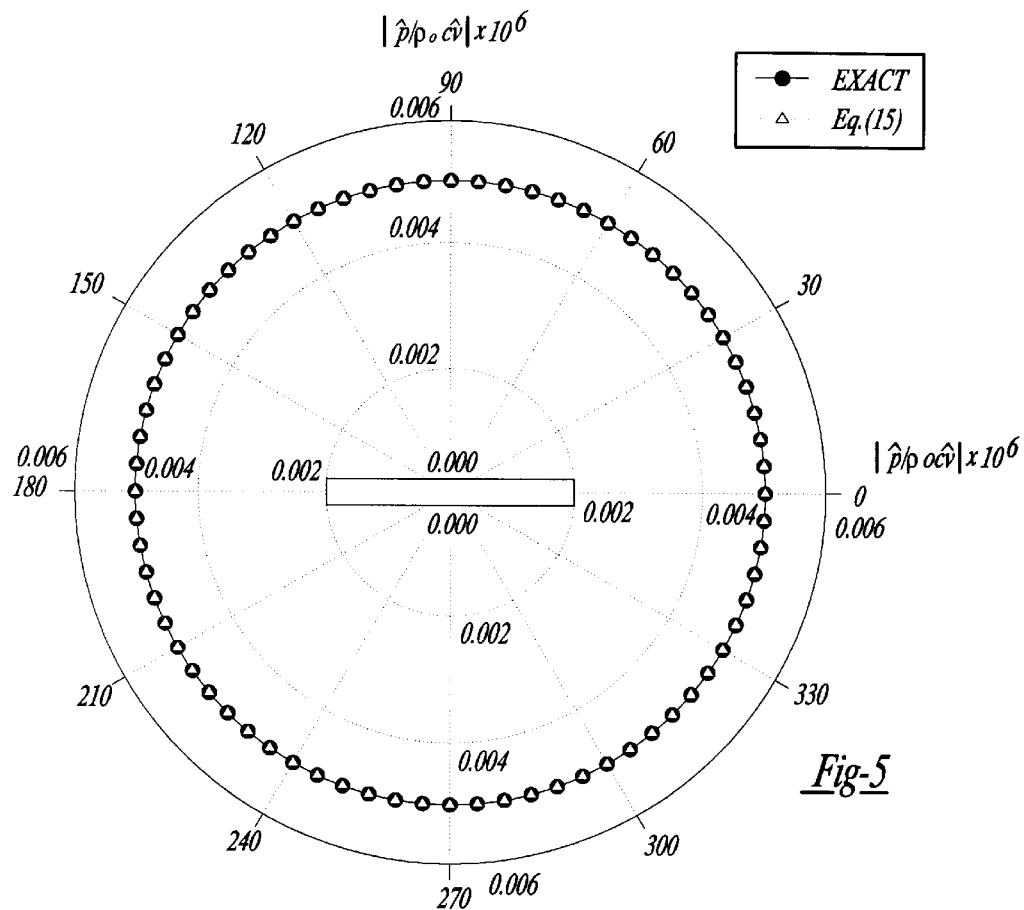
FIG. 5 is a comparison of the radiation pattern of the dimensionless field acoustic pressure give by Eq. (15), and the exact solution.

FIG. 4 demonstrates the comparisons of the real and imaginary parts of the dimensionless acoustic pressure obtained by using Eq. (14) with those of a monopole at kb=1 along the generator of the cylindrical surface. Here the abcisa represents a dimensionless distance s/a along the generator of the cylindrical surface. In particular, s/a=0 indicates the center of the side wall, s/a=±10 the edges that separate the side wall from the flat end, and s/a=±11 the centers of the two ends. FIG. 5 shows the comparison of the radiation pattern of the dimensionless field acoustic pressure given by Eq. (15) at a radial distance of r=20(m) with that of the monopole source.

Figure 6A:
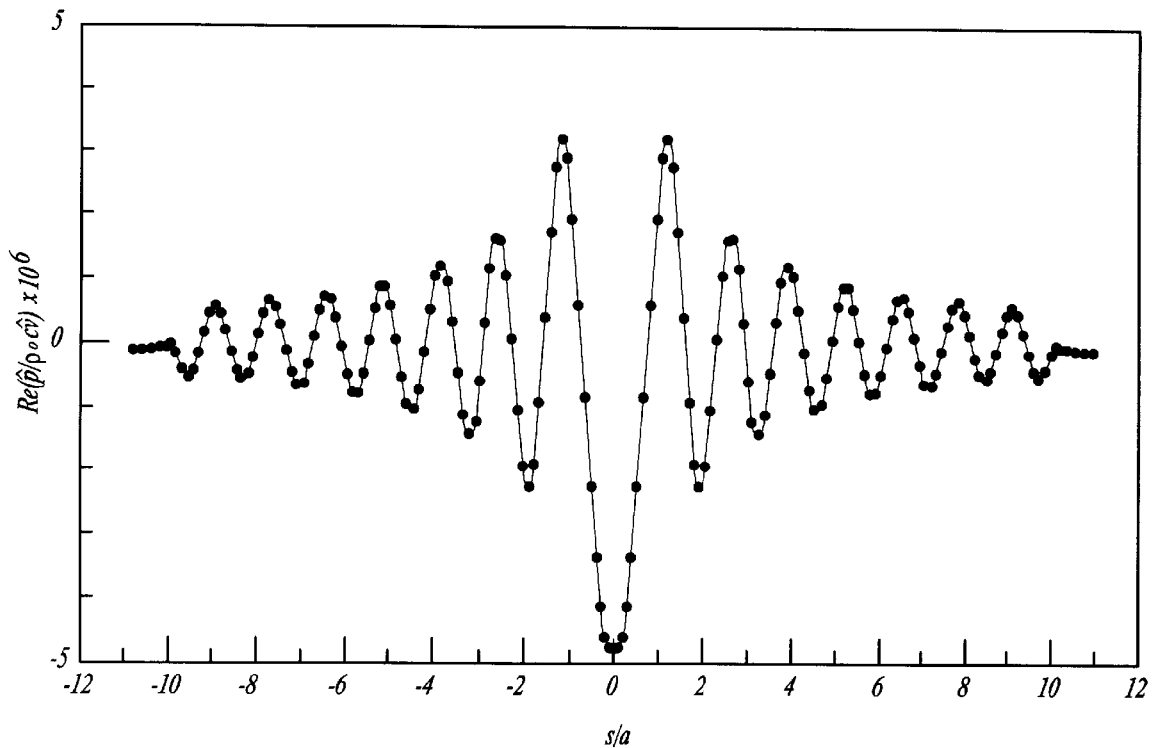
FIG. 6a is a comparison of the dimensionless acoustic pressure given by Eq. (14), real part, and the exact solution.
Figure 6B:
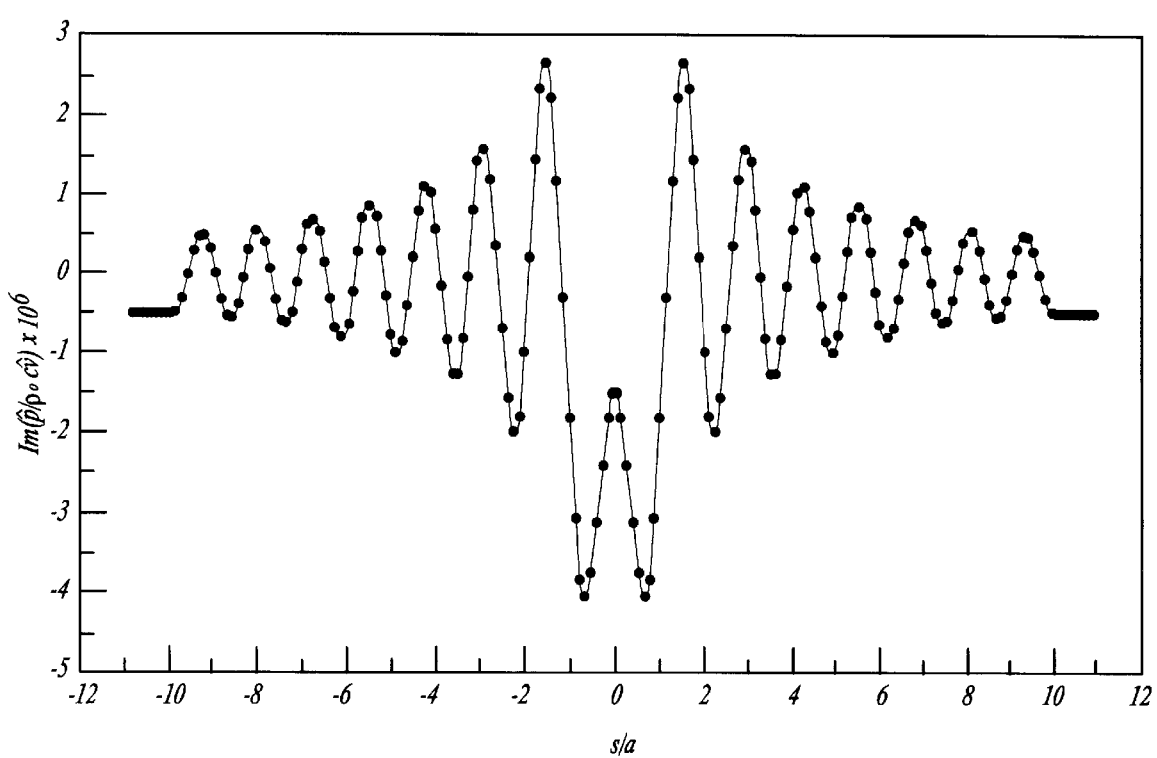
FIG. 6b is a comparison of the dimensionless acoustic pressure given by Eq. (14), imaginary part, and the exact solution.
Figure 7:
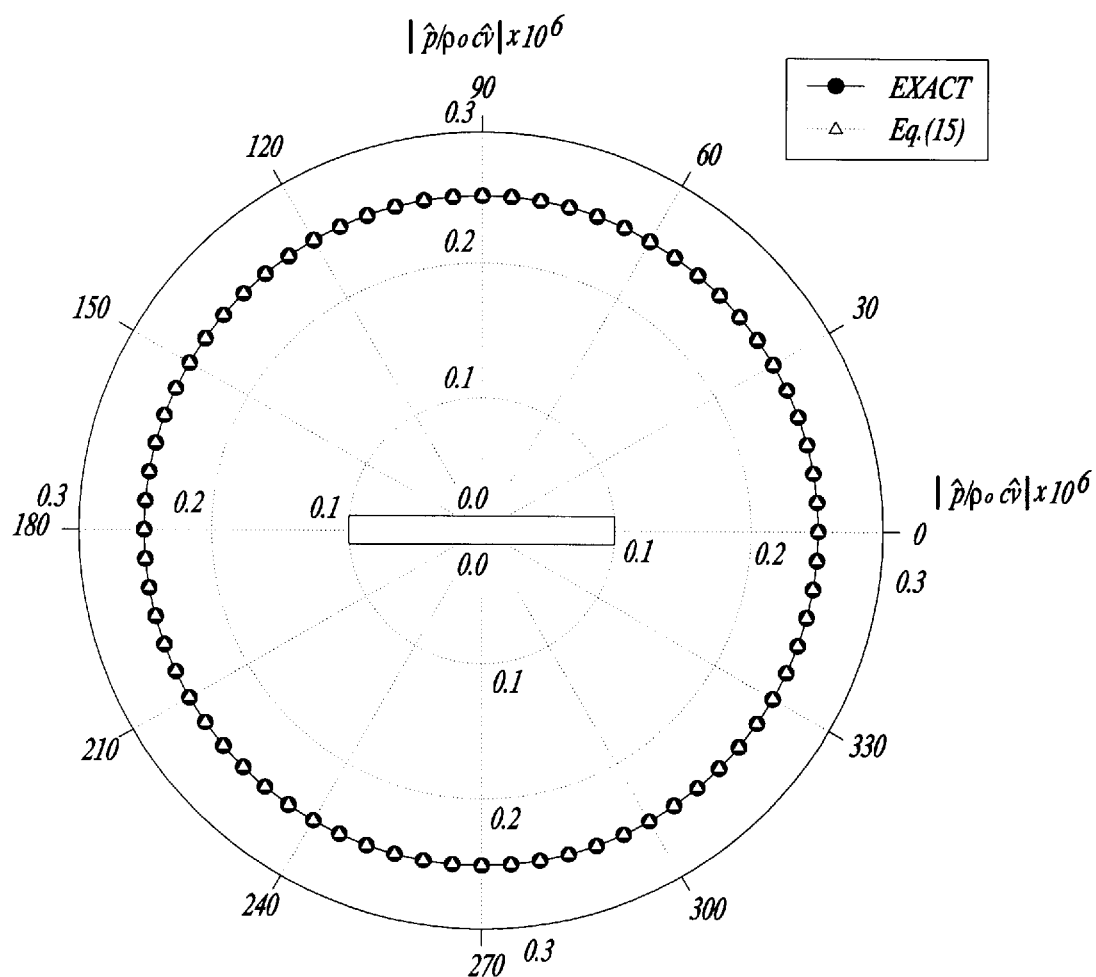
FIG. 7 is a comparison of the radiation pattern of the dimensionless field acoustic pressure given by Eq. (15), and the exact solution.

In a similar manner, we calculate the surface and field acoustic pressure by using Eqs. (14) and (15) at kb=50, and compare the results thus obtained with those of the monopole source (see FIGS. 6 and 7).

Figure 8A:
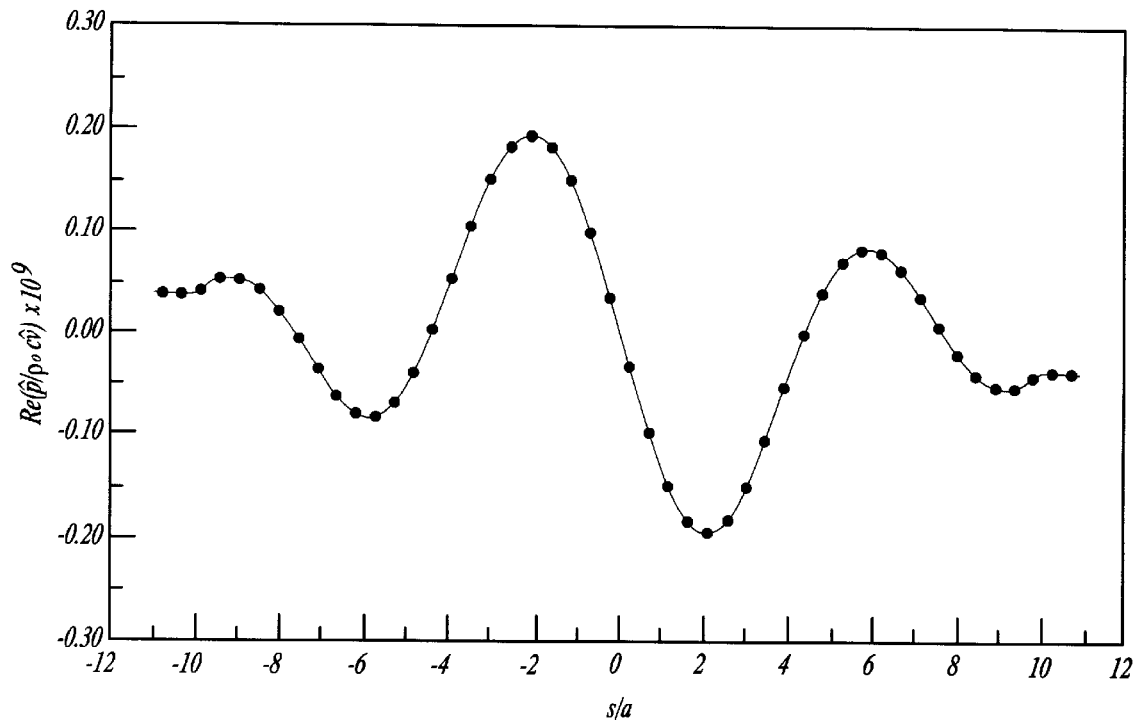
FIG. 8a is a comparison of the dimensionless acoustic pressure given by Eq. (14), real part, and the exact solution.
Figure 8B:
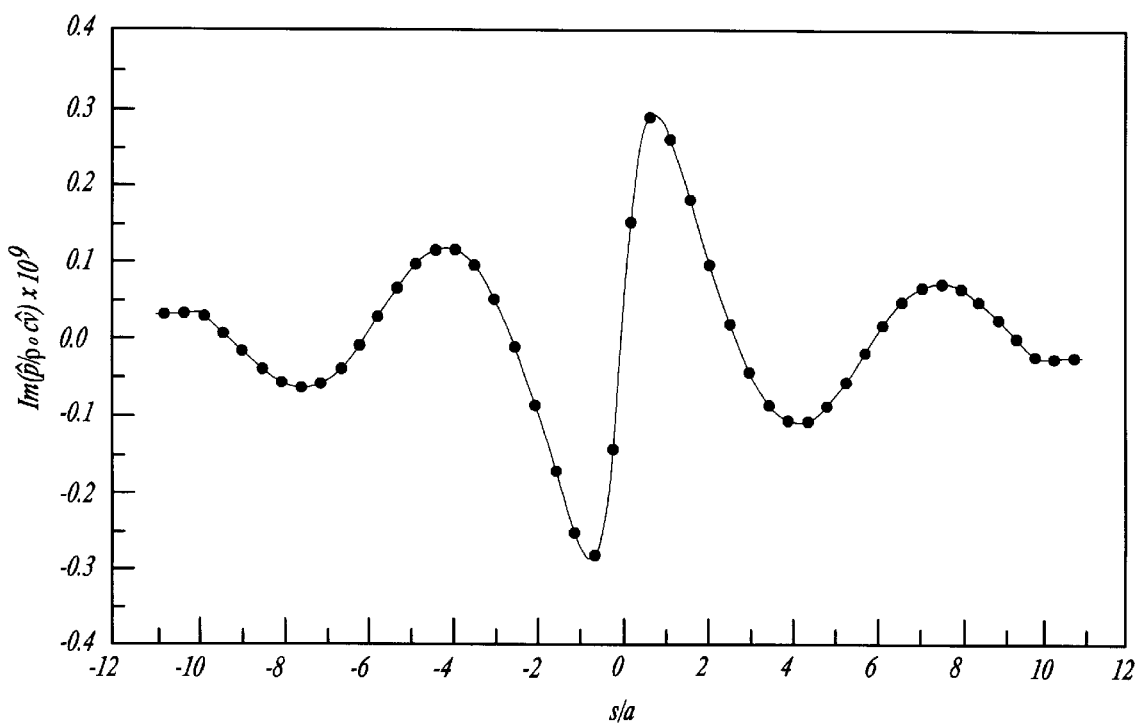
FIG. 8b is a comparison of the dimensionless acoustic pressure given by Eq. (14), imaginary part, and the exact solution.
Figure 9:
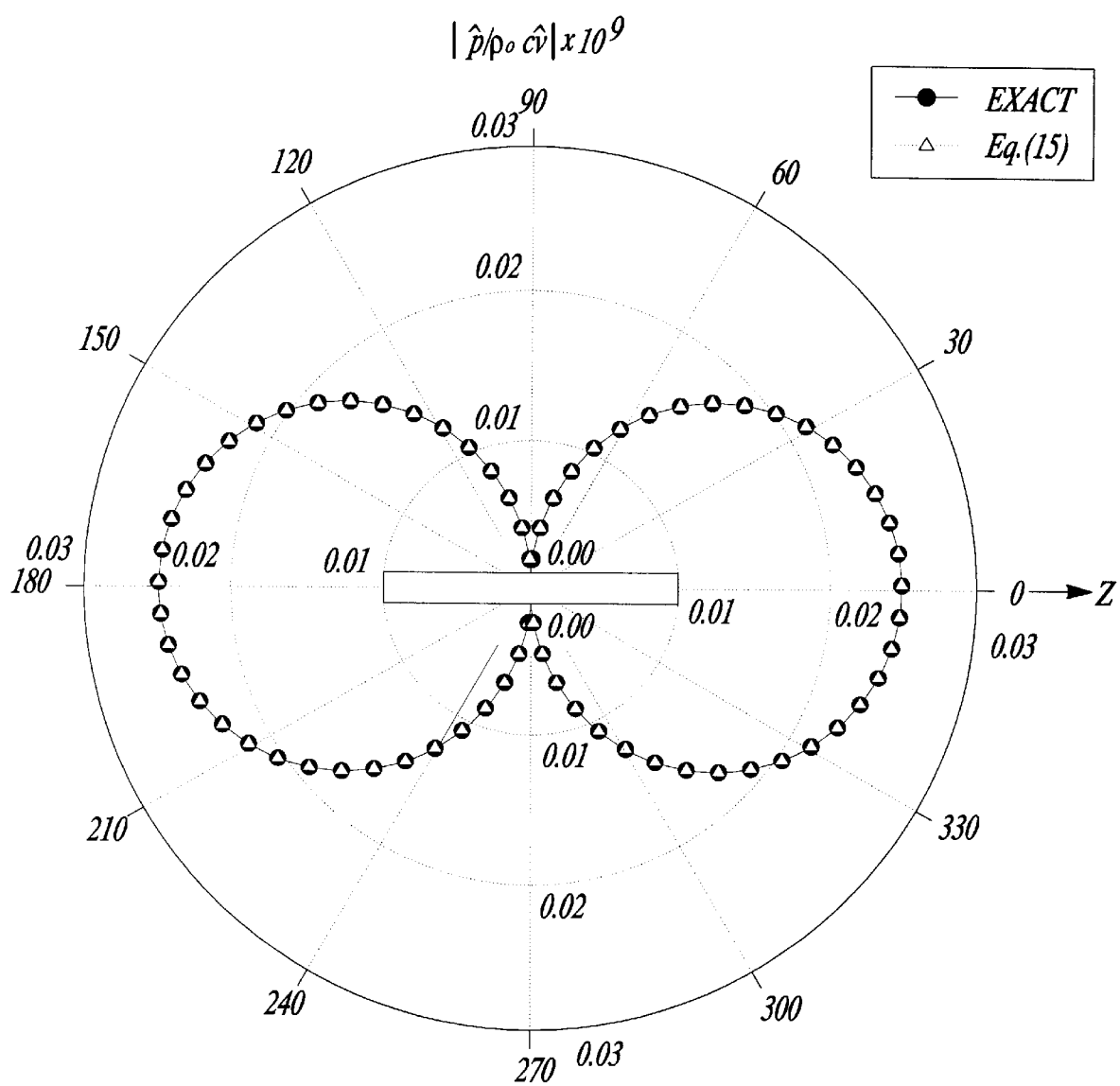
FIG. 9 is a comparison of the radiation pattern of the dimensionless field acoustic pressure given by Eq. (15), and the exact solution.
Figure 10A:
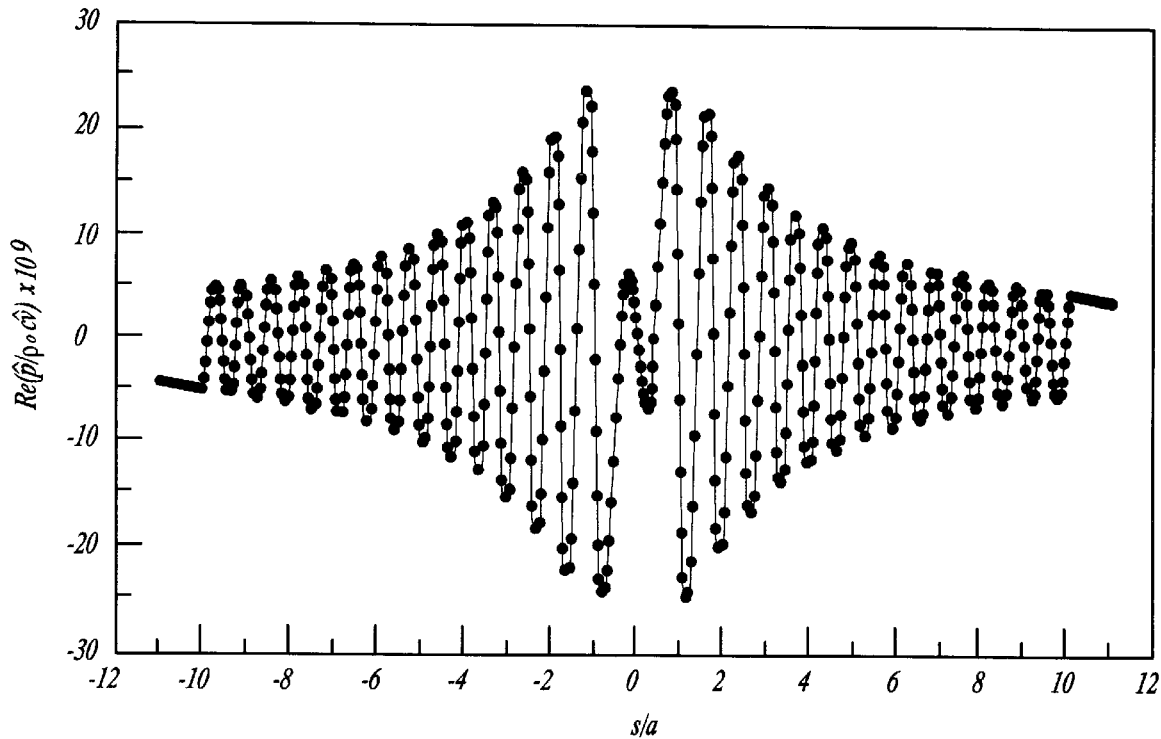
FIG. 10a is a comparison of the dimensionless acoustic pressure given by Eq. (14), real part, and the exact solution.
Figure 10B:
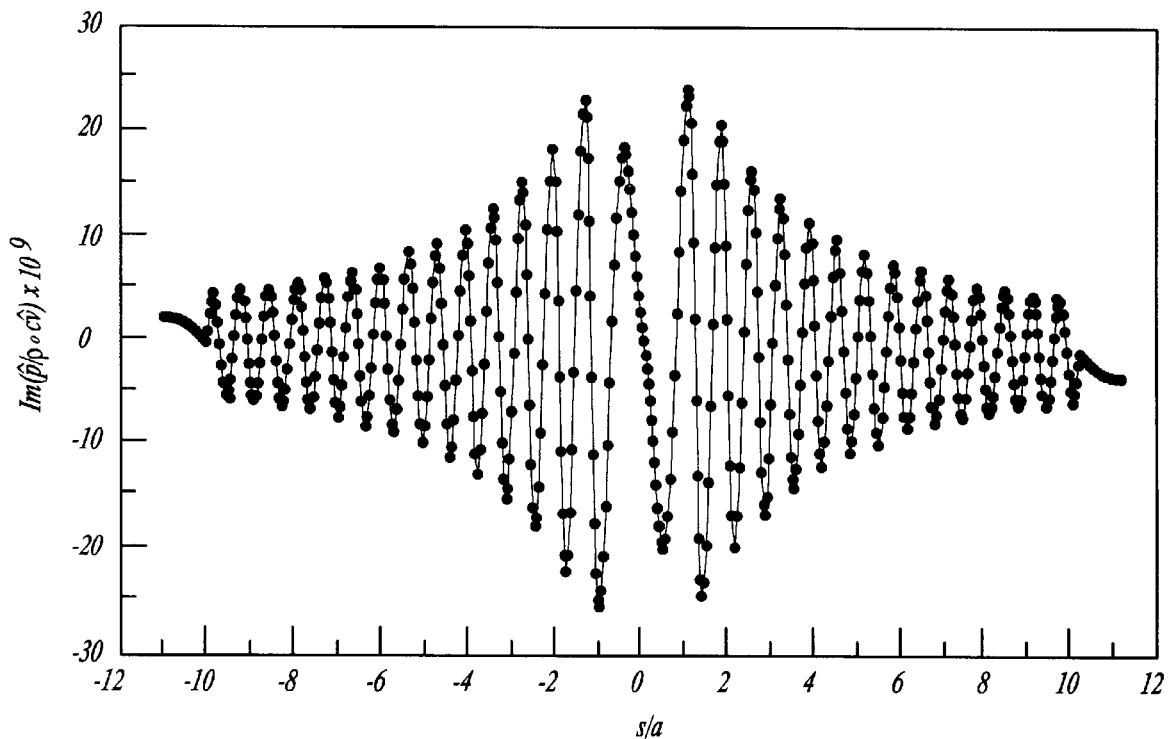
FIG. 10b is a comparison of the dimensionless acoustic pressure given by Eq. (14), imaginary part, and the exact solution.
Figure 11:
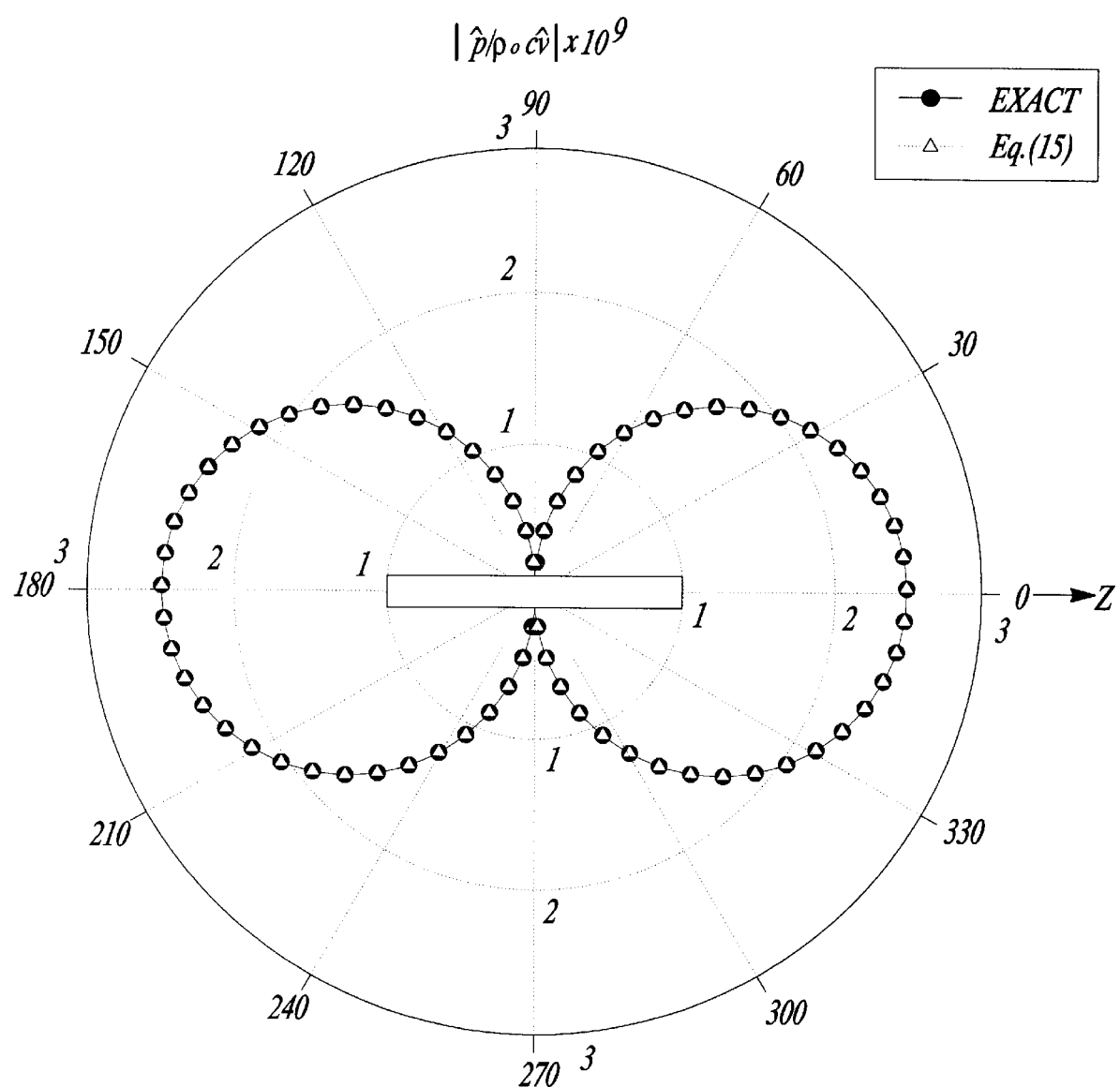
FIG. 11 is a comparison of the radiation pattern of the dimensionless field acoustic pressure given by Eq. (15), and the exact solution.

Next, we repeat the same procedures and compare the calculated surface and field acoustic pressures with those of a dipole at kb=10 and 100. Because of the increase in the excitation frequency, we double the number of discretization segments. Specifically, we use 960 rings on the side wall and 48 rings on each end, and 96 segments along the azimuth within each of these rings. The comparisons of the real and imaginary parts of the surface acoustic pressure for kb=10 are depicted in FIG. 8, and those of the filed acoustic pressure are displayed in FIG. 9. FIGS. 10 and 11 demonstrate the comparisons of the surface and field acoustic pressures for kb=100.

In accordance with the provisions of the patent statutes, the present invention has been described in what is considered to represent a preferred embodiment. However, it should be noted that the invention can be practiced otherwise than as specifically illustrated and described without departing from its spirit or scope.

What is claimed is:

1. A method for predicting sound radiation from a vibrating object including the steps of:
   a) defining a surface of the vibrating object;
   b) determining the particle velocity at the surface of the vibrating object;
   c) integrating the particle velocity over the surface of the vibrating object;
   d) determining the acoustic pressure at points other than at the surface of the object based upon the integration of the particle velocity over the surface of the vibrating object.

2. The method for predicting sound radiation from a vibrating object according to claim 1 wherein said step a) further includes the step of measuring the particle velocity at the surface of the vibrating object utilizing an accelerometer.

3. The method for predicting sound radiation from a vibrating object according to claim 1 further including the steps of:
   determining the normal and tangential components of the particle velocity at the surface of the vibrating object.

4. The method for predicting sound radiation from a vibrating object according to claim 3 further including the step of:
integrating the normal and tangential components of the particle velocity over the surface of the vibrating object.

5. The method for predicting sound radiation from a vibrating object according to claim 3 further including the step of using a non-intrusive laser Doppler velocimeter.

6. The method for predicting sound radiation from a vibrating object according to claim 1 further including the step of utilizing Gaussian quadratures to solve the integral of velocity distribution over said surface of said object.

7. The method for predicting sound radiation from a vibrating object according to claim 1 wherein said step c) is performed according to the equation:

$$\hat{p}(\vec{x}) = \mathcal{L}_1(\hat{v}_\eta) + \mathcal{L}_2(\hat{v}_n) \tag{15}$$

where $\mathcal{L}_{1,2}$ represent the integral operators operating on the tangential and normal components of the particle velocity, respectively, $$\mathcal{L}_1(\hat{v}_\eta) = \frac{i\omega\rho_0}{4\pi} \int_S \left\{ \frac{\partial G(\vec{x}|\vec{x}_S)}{\partial n} \left[ \int_{S'} \frac{\partial G(\vec{x}_S|\vec{x}_{S'})}{\partial n_{S'}} \left( \int_{(\vec{x}'_S \to \vec{x}_S)} \hat{v}_\eta(\vec{x}_S) d\eta \right) dS' \right] \times \left[ 2\pi - \int_{S'} \frac{\partial G(\vec{x}_S|\vec{x}_{S'})}{\partial n_{S'}} dS' \right]^{-1} \right\} dS + \frac{i\omega\rho_0}{4\pi} \int_S \frac{\partial G(\vec{x}|\vec{x}_S)}{\partial n} \left( \int_{(\vec{x}'_S \to \vec{x}_S)} \hat{v}_\eta(\vec{x}_S) d\eta \right) dS \tag{16a}$$

$$\mathcal{L}_2(\hat{v}_n) = -\frac{i\omega\rho_0}{4\pi} \int_S \left\{ \frac{\partial G(\vec{x}|\vec{x}_S)}{\partial n} \left[ \int_{S'} \hat{v}_n(\vec{x}_{S'}) G(\vec{x}_S|\vec{x}_{S'}) dS' \right] \times \left[ 2\pi - \int_{S'} \frac{\partial G(\vec{x}_S|\vec{x}_{S'})}{\partial n_{S'}} dS' \right]^{-1} \right\} dS - \frac{i\omega\rho_0}{4\pi} \int_S \hat{v}_n(\vec{x}_S) G(\vec{x}|\vec{x}_S) dS \tag{16b}$$

8. The method for predicting transient sound radiation from a vibrating object according to claim 1 further including the steps of:
   taking the inverse Fourier transform of the acoustic pressure; and
   calculating transient acoustic radiation from said object.

9. The method for predicting sound radiation from a vibrating object according to claim 1 further including the step of calculating an acoustic pressure at a point enclosed by the surface of the vibrating object.

10. The method for predicting sound radiation interior to a vibrating object according to claim 1 wherein said step c) is performed according to the equation:

$$\hat{p}(\vec{X}) = \mathcal{L}_1^{int}\{\hat{v}_\eta\} + \mathcal{L}_2^{int}\{\hat{v}_n\} \tag{17}$$

where $\mathcal{L}^{int}_{1,2}$ represent the integral operators operating on the tangential and normal components of the particle velocity, respectively, $$\mathcal{L}_1^{int}\{\hat{v}_\eta\} = \frac{i\omega\rho_0}{4\pi} \int_S \left\{ \frac{\partial G(\vec{X}|\vec{X}_S)}{\partial n_S} \left[ \int_{S'} \frac{\partial G(\vec{X}_S|\vec{X}_{S'})}{\partial n_{S'}} \left( \int_{(\vec{x}'_{S'} \to \vec{x}_{S'})} \hat{v}_\eta(\vec{X}_S) d\eta \right) dS' \right] \times \left[ 2\pi + \int_{S'} \frac{\partial G(\vec{X}_S|\vec{X}_{S'})}{\partial n_{S'}} dS' \right]^{-1} \right\} dS - \frac{i\omega\rho_0}{4\pi} \int_S \frac{\partial G(\vec{X}|\vec{X}_S)}{\partial n_S} \left( \int_{(\vec{X}'_S \to \vec{X}_S)} \hat{v}_\eta(\vec{X}_S) d\eta \right) dS \tag{18a}$$

$$\mathcal{L}_2^{int}\{\hat{v}_\eta\} = -\frac{i\omega\rho_0}{4\pi}\int_S\left\{\frac{\partial G(\vec{X}|\vec{X}_S)}{\partial n_S}\left[\int_{S'}\hat{v}_n(\vec{x}_S)G(\vec{x}_S|\vec{s}_{S'})dS'\right]\times\left[2\pi+\int_{S'}\frac{\partial G(\vec{x}_S|\vec{x}_{S'})}{\partial n_{S'}}dS'\right]^{-1}\right\}dS+\frac{i\omega\rho_0}{4\pi}\int_S\hat{v}_n(\vec{x}_S)G(\vec{X}|\vec{X}_S)dS \qquad (18b)$$

11. The method for predicting sound radiation from a vibrating object according to claim 1 wherein said vibrating object is a finite object in free space.

12. The method for predicting sound scattering from an object according to claim 11 wherein said step c) is performed according to the equation:

$$\hat{p}^{sca}(\vec{x}) = \mathcal{L}_1\{\hat{v}_\eta^{total}\} + \mathcal{L}_2\{\hat{v}_n^{total}\} \qquad (19)$$

where $\mathcal{L}_{1,2}$ represent the integral operators operating on the tangential and normal components of the particle velocity, respectively, 15. A system for predicting sound radiation from a vibrating object including:

a) a computer having an input device for defining a surface of the vibrating object;

b) means for determining the particle velocity at the surface of the vibrating object;

c) means for integrating the particle velocity over the surface of the vibrating object;

$$\mathcal{L}_1(\hat{v}_\eta) = \frac{i\omega\rho_0}{4\pi}\int_S\left\{\frac{\partial G(\vec{x}|\vec{x}_S)}{\partial n}\left[\int_{S'}\frac{\partial G(\vec{x}_S|\vec{x}_{S'})}{\partial n_{S'}}\left(\int_{(\vec{x}'_S\to\vec{x}_S)}\hat{v}_\eta(\vec{x}_{S'})d\eta\right)dS'\right]\times\left[2\pi-\int_{S'}\frac{\partial G(\vec{x}_S|\vec{x}_{S'})}{\partial n_{S'}}dS'\right]^{-1}\right\}dS+\frac{i\omega\rho_0}{4\pi}\int_S\frac{\partial G(\vec{x}|\vec{x}_S)}{\partial n}\left(\int_{(\vec{x}'_S\to\vec{x}_S)}\hat{v}_\eta(\vec{x}_S)d\eta\right)dS \qquad (16a)$$

$$\mathcal{L}_2(\hat{v}_\eta) = -\frac{i\omega\rho_0}{4\pi}\int_S\left\{\frac{\partial G(\vec{x}|\vec{x}_S)}{\partial n}\left[\int_{S'}\hat{v}_n(\vec{x}_S)G(\vec{x}_S|\vec{s}_{S'})dS'\right]\times\left[2\pi-\int_{S'}\frac{\partial G(\vec{x}_S|\vec{x}_{S'})}{\partial n_{S'}}dS'\right]^{-1}\right\}dS-\frac{i\omega\rho_0}{4\pi}\int_S\hat{v}_n(\vec{x}_S)G(\vec{x}|\vec{x}_S)dS \qquad (16b)$$

$\hat{v}_\eta^{total}$ and $\hat{v}_n^{total}$ represent the components of the total particle velocity normal and tangential to the surface of the object, respectively, $$\hat{v}_\eta^{total} = (\hat{v}^{sca}+\hat{v}^{inc})\bullet\vec{e}_\eta \qquad (20A)$$

$$\hat{v}_n^{total} = (\hat{v}^{sca}+\hat{v}^{inc})\bullet\vec{e}_n \qquad (20C)$$

where $\hat{v}^{sca}$ and $\hat{v}^{int}$ are the scattered and incident components of the particle velocity, respectively, and $\vec{e}_\eta$ and $\vec{e}_n$ represent the unit vectors in the tangential and normal directions at the surface of the object, respectively.

13. The method for predicting sound scattering from an object according to claim 1 wherein said vibrating object is a finite object in half space bounded by a baffle.

14. The method for predicting sound radiation from a vibrating object according to claim 13 wherein step c) is performed according to the equation:

$$\hat{p}^{sca}(\vec{x}) = \mathcal{L}_3\{\hat{v}_\eta^{total}\} + \mathcal{L}_4\{\hat{v}_n^{total}\} \qquad (21)$$

where $\mathcal{L}_{3,4}$ are given by d) means for determining the acoustic pressure at points other than at the surface of the object based upon the integration of the particle velocity over the surface of the vibrating object.

16. The system for predicting sound radiation from a vibrating object according to claim 15 further including a sensor generating a signal indicative of said particle velocity.

17. The system for predicting sound radiation from a vibrating object according to claim 15 wherein said sensor is a non-intrusive laser Doppler velocimeter.

18. The system for predicting sound radiation from a vibrating object according to claim 15 wherein said means for integrating integrates the particle velocity over the surface of the object according to:

$$\hat{p}(\vec{x}) = \mathcal{L}_1(\hat{v}_\eta) + \mathcal{L}_2(\hat{v}_n) \qquad (15)$$

where $\mathcal{L}_{1,2}$ represent the integral operators operating on the tangential and normal components of the particle velocity, respectively, $$\mathcal{L}_3\{\hat{v}_\eta^{total}\} = \frac{i\omega\rho_0}{4\pi}\int_S\left\{\frac{\partial G(\vec{x}|\vec{x}_S)}{\partial n_S}\left[\int_{S'}\frac{\partial G(\vec{x}_S|\vec{x}_{S'})}{\partial n_{S'}}\left(\int_{(\vec{x}'_S\to\vec{x}_S)}\hat{v}_\eta^{total}(\vec{x}_{S'})d\eta\right)dS'\right]\times\left[2\pi-\int_{S'}\frac{\partial G(\vec{x}_S|\vec{x}_{S'})}{\partial n_{S'}}dS'\right]^{-1}\right\}dS+\frac{i\omega\rho_0}{4\pi}\int_S\frac{\partial G(\vec{x}|\vec{x}_S)}{\partial n_S}\left(\int_{(\vec{x}'_S\to\vec{x}_S)}\hat{v}_\eta^{total}(\vec{x}_S)d\eta\right)dS \qquad (22a)$$

$$\mathcal{L}_4\{\hat{v}_\eta^{total}\} = -\frac{i\omega\rho_0}{4\pi}\int_S\left\{\frac{\partial G(\vec{x}|\vec{x}_S)}{\partial n_S}\left[\int_{S'}\hat{v}_n^{total}(\vec{x}_S)G(\vec{x}_S|\vec{s}_{S'})dS'\right]\times\left[2\pi-\int_{S'}\frac{\partial G(\vec{x}_S|\vec{x}_{S'})}{\partial n_{S'}}dS'\right]^{-1}\right\}dS-\frac{i\omega\rho_0}{4\pi}\int_S\hat{v}_n^{total}(\vec{x}_S)G(\vec{x}|\vec{s}_S)dS \qquad (22b)$$

$$\mathfrak{L}_1(\hat{v}_\eta) = \frac{i\omega\rho_0}{4\pi} \int_S \left\{ \frac{\partial G(\vec{x}|\vec{x}_S)}{\partial n} \left[ \int_{S'} \frac{\partial G(\vec{x}_S|\vec{x}_{S'})}{\partial n_{S'}} \left( \int_{(\vec{x}'_S \to \vec{x}_{S'})} \hat{v}_\eta(\vec{x}_S) d\eta \right) dS' \right] \times \right.$$

$$\left. \left[ 2\pi - \int_{S'} \frac{\partial G(\vec{x}_S|\vec{x}_{S'})}{\partial n_{S'}} dS' \right]^{-1} \right\} dS + \frac{i\omega\rho_0}{4\pi} \int_S \frac{\partial G(\vec{x}|\vec{x}_S)}{\partial n} \left( \int_{(\vec{x}'_S \to \vec{x}_S)} \hat{v}_\eta(\vec{x}_S) d\eta \right) dS \quad (16a)$$

$$\mathfrak{L}_2(\hat{v}_\eta) = -\frac{i\omega\rho_0}{4\pi} \int_S \left\{ \frac{\partial G(\vec{x}|\vec{x}_S)}{\partial n} \left[ \int_{S'} \hat{v}_n(\vec{x}_S) G(\vec{x}_S|\vec{x}_{S'}) dS' \right] \times \left[ 2\pi - \int_{S'} \frac{\partial G(\vec{x}_S|\vec{x}_{S'})}{\partial n_{S'}} dS' \right]^{-1} \right\} dS - \frac{i\omega\rho_0}{4\pi} \int_S \hat{v}_n(\vec{x}_S) G(\vec{x}|\vec{x}_S) dS \quad (16b)$$

\* \* \* \* \*

UNITED STATES PATENT AND TRADEMARK OFFICE
CERTIFICATE OF CORRECTION

PATENT NO. : 5,886,264
DATED : March 23, 1999
INVENTOR(S) : Hu Quiang and Sean F. Wu It is certified that error appears in the above-identified patent and that said Letters Patent is hereby corrected as shown below:

<u>Title page,</u>
Item [75], Inventors, "Quiang Hu" should be -- Hu Quiang --.

Signed and Sealed this

Twenty-seventh Day of August, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 5,886,264
DATED         : March 23, 1999
INVENTOR(S)   : Qiang Hu and Sean F. Wu It is certified that error appears in the above-identified patent and that said Letters Patent is hereby corrected as shown below:

Title page,
Item [75], Inventors, "Quiang Hu" should be -- Qiang Hu --.

Signed and Sealed this

Twentieth Day of September, 2005

JON W. DUDAS
*Director of the United States Patent and Trademark Office*